United States Patent
Kang et al.

(10) Patent No.: US 10,697,838 B1
(45) Date of Patent: Jun. 30, 2020

(54) FLEXIBLE FILTER ELEMENT USING LIQUID METAL AND METHOD OF PREPARING THE SAME

(71) Applicant: KOREA INSTITUTE OF INDUSTRIAL TECHNOLOGY, Cheonan-si, Chungcheongnam-do (KR)

(72) Inventors: Sung Bok Kang, Yongin-si (KR); Jong Seok Kim, Ansan-si (KR); Hyeun Seog Choi, Yongin-si (KR)

(73) Assignee: KOREA INSTITUTE OF INDUSTRIAL TECHNOLOGY, Cheonan-si (KR)

( * ) Notice: Subject to any disclaimer, the term of this patent is extended or adjusted under 35 U.S.C. 154(b) by 0 days.

(21) Appl. No.: 16/397,073

(22) Filed: Apr. 29, 2019

(30) Foreign Application Priority Data

Apr. 15, 2019 (KR) .......................... 10-2019-0043806

(51) Int. Cl.
| | |
|---|---|
| *G01L 1/14* | (2006.01) |
| *G01B 7/16* | (2006.01) |
| *H01H 29/28* | (2006.01) |
| *H01B 1/22* | (2006.01) |
| *A61B 5/053* | (2006.01) |

(52) U.S. Cl.
CPC ............... *G01L 1/14* (2013.01); *G01B 7/16* (2013.01); *H01B 1/22* (2013.01); *H01H 29/28* (2013.01); *A61B 5/0531* (2013.01)

(58) Field of Classification Search
CPC ... G01L 1/14; G01B 7/16; H01B 1/22; H01H 29/28; A61B 5/0531
USPC ........................................................ 73/774
See application file for complete search history.

(56) References Cited

U.S. PATENT DOCUMENTS

| 6,320,639 B1* | 11/2001 | Mori ................. G02F 1/133514 |
| | | 349/155 |
| 8,826,747 B2 | 9/2014 | Lee et al. |
| 9,945,739 B2 | 4/2018 | Jeon et al. |

(Continued)

FOREIGN PATENT DOCUMENTS

| CN | 105938021 A | 9/2016 |
| KR | 100771781 B1 | 10/2007 |

(Continued)

OTHER PUBLICATIONS

Sungbok Kang et al., "Fabrication of Flexible Passive Elements on Papers Using Liquid Eutectic Gain Patterns", ENGE 2018, The 5th international Conference of Electronic Materials and Nanotechnology for Green Environment, Nov. 11-14, 2018, Korea.

(Continued)

*Primary Examiner* — Max H Noori
(74) *Attorney, Agent, or Firm* — Cantor Colburn LLP

(57) ABSTRACT

Provided are a filter element and a method of preparing a filter element. The filter element includes a pattern substrate having a first channel formed on one surface and a second channel formed on the other surface and including a first base and a second base which have different liquid permeabilities; a first liquid metal pattern disposed in the first channel; a second liquid metal pattern disposed in the second channel and at least partially overlapping the first liquid metal pattern; and a contactor configured to invade in the first base and the second base and electrically connect the first liquid metal pattern to the second liquid metal pattern.

17 Claims, 20 Drawing Sheets

(56) References Cited

U.S. PATENT DOCUMENTS

| | | | |
|---|---|---|---|
| 10,184,779 B2 | 1/2019 | Norisada et al. | |
| 2010/0308334 A1* | 12/2010 | Choi | H01L 27/1214 257/59 |
| 2012/0127457 A1* | 5/2012 | Hayama | G02F 1/1309 356/51 |
| 2015/0348996 A1* | 12/2015 | Qin | H01L 27/1214 257/43 |
| 2018/0192911 A1 | 7/2018 | Jung et al. | |
| 2019/0003818 A1 | 1/2019 | Asaka et al. | |
| 2019/0243201 A1* | 8/2019 | Li | G02F 1/13306 |

FOREIGN PATENT DOCUMENTS

| | | |
|---|---|---|
| KR | 101543628 B1 | 8/2015 |
| KR | 101595824 B1 | 2/2016 |
| KR | 101791016 B1 | 10/2017 |
| KR | 1020180118030 A | 10/2018 |
| KR | 1020190015914 A | 2/2019 |

OTHER PUBLICATIONS

Shanliangzi Liu et al., "Design and characterization of a single channel two-liquid capacitor and its application to hyperelastic strain sensing," Lab on a Chip, Jan. 2015, pp. 1376-1384, vol. 15, The Royal Society of Chemistry.

Xiaoguang Liu et al., "MEMS Liquid Metal Through-wafer Microstrip to Microstrip Transition," IEEE MTT-S International Microwave Symposium, 2008, pp. 41-44.

* cited by examiner

Example 1-1 (Inductor Element)

Example 1-2 (Capacitor Element)

Comparative Example 1 (Inductor Element)

Comparative Example 2 (Capacitor Element)

FLEXIBLE FILTER ELEMENT USING LIQUID METAL AND METHOD OF PREPARING THE SAME

CROSS-REFERENCE TO RELATED APPLICATION

This application claims priority from Korean Patent Application No. 10-2019-0043806, filed on Apr. 15, 2019, in the Korean Intellectual Property Office, and all the benefits accruing therefrom under 35 U.S.C. 119, the disclosure of which in its entirety is herein incorporated by reference.

BACKGROUND

1. Field of the Disclosure

The present invention relates to a flexible filter element using a liquid metal and a method of preparing the same, and more particularly, to a flexible filter element with improved electrical connection between an inductor element and a capacitor element and a method of preparing the same.

2. Discussion of Related Art

Recently, various sensor devices are being developed due to the development of Internet of Things (IoT) technology. For example, a living body monitoring device attached to a living thing such as an animal or a human may be attached to a body surface to measure body fluid components, collect body temperature information, heartbeat information, position information, and a variety of other information, thereby managing physical activity based on the collected information. Alternatively, a food safety monitoring device attached to a food product may collect information on distribution history and quality of the food product, thereby securing food stability and contributing to public health improvement.

Such sensor devices should satisfy various characteristics according to surfaces on which these sensor devices will be provided. In a case in which a sensor device is the above-described living body monitoring device or the above-described food safety monitoring device, when a target surface to which the sensor device will be attached is a curved surface and the target surface is also fluid such that adhesion between the target surface and the sensor device is poor, there may occur a problem in that sensing sensitivity is significantly degraded. Therefore, it is urgent to develop technology for implementing a sensor device with complete flexibility.

A pressure and temperature sensor using an amorphous metal is disclosed in Patent Document 1 (U.S. Pat. No. 9,945,739 B2). Specifically, a sensor device with a stretchable characteristic which is capable of being used for an electronic skin is disclosed in Patent Document 1. In Patent Document 1, in order to implement a flexible sensor, a wiring of the sensor device is formed using an amorphous metal and an alloy thereof. However, the sensor device of Patent Document 1 is also limited to merely employing a metal layer with improved flexibility such that there is still a problem in that the wiring is damaged when the degree of bending of the sensor device is large or when the sensor device is completely folded.

A stretchable electrode and a sensor sheet which are used in a stretchable sensor for a medical material employed in an artificial muscle or an artificial skin are disclosed in Patent Document 2 (U.S. Pat. No. 10,184,779 B2). Patent Document 2 instructs formation of an electrode body through a fiber using a multi-layer carbon nanotube. However, even though an electrode can be formed locally, using the carbon nanotube of Patent Document 2, it is extremely difficult to form a wiring and the like.

In addition to the above description, various attempts have been made to implement a flexible sensor device as disclosed in Patent Document 3 (U.S. Pat. No. 8,826,747 B2), Patent Document 4 (U.S. Patent Application Publication No. 2019-0003818 A1), and Patent Document 5 (U.S. Patent Application Publication No. 2018-0192911 A1).

PATENT DOCUMENT (Patent Document 1) U.S. Pat. No. 9,945,739 B2 (Apr. 17, 2018)

(Patent Document 2) U.S. Pat. No. 10,184,779 B2 (Jan. 22, 2019)

(Patent Document 3) U.S. Pat. No. 8,826,747 B2 (Sep. 9, 2014)

(Patent Document 4) U.S. Patent Application Publication No. 2019-0003818 A1 (Jan. 3, 2019)

(Patent Document 5) U.S. Patent Application Publication No. 2018-0192911 A1 (Jul. 12, 2018)

SUMMARY

Meanwhile, an electronic device such as a sensor is composed of an electronic circuit configured using various active and passive elements. For example, the electronic device may include a filter element such as a high-pass filter (HPF) and/or a low-pass filter (LPF). In particular, in the case of a filter element for transmitting only a specific frequency band or blocking transmission of the specific frequency band, stability of a wiring constituting the filter element may be a very important factor. For example, when the wiring of the filter element is partially damaged or deformed, the filter element may not exhibit a stable characteristic, and further, significant degradation in performance of an electronic device such as a sensor device may occur entirely.

The present invention is directed to providing a filter element which is capable of exhibiting flexibility. At the same time, the present invention is directed to providing a filter element which is capable of improving an electrical connection between passive elements to form a stable structure.

The present invention is also directed to providing a method of preparing a filter element exhibiting flexibility and having an improved electrical connection. Further, the present invention is directed to providing a method of preparing a filter element, which reduces a manufacturing cost and has a simplified manufacturing process.

It should be noted that objects of the present disclosure are not limited to the above-described objects, and other objects of the present disclosure will be apparent to those skilled in the art from the following descriptions.

According to an exemplary embodiment of the invention, there is provided a filter element. The filter element comprises, a pattern substrate having a first channel formed on one surface and a second channel formed on the other surface and including a first base and a second base which have different liquid permeabilities; a first liquid metal pattern disposed in the first channel; a second liquid metal pattern disposed in the second channel and at least partially overlapping the first liquid metal pattern; and a contactor configured to invade in the first base and the second base and electrically connect the first liquid metal pattern to the second liquid metal pattern.

In an exemplary embodiment, the contactor may be electrically equivalent to an output terminal of the filter element; and a width of the contactor may decrease in a direction from the first liquid metal pattern to the second liquid metal pattern.

In an exemplary embodiment, the filter element may be a low-pass filter element; the first liquid metal pattern forms an inductor element; and the second liquid metal pattern forms a capacitor element.

In an exemplary embodiment, the filter element may be a high-pass filter element; the first liquid metal pattern forms a capacitor element; and the second liquid metal pattern forms an inductor element.

In an exemplary embodiment, the first base may be in contact with the first liquid metal pattern; the second base may be in contact with the second liquid metal pattern; the contactor may include: a first contactor configured to invade in the first base; and a second contactor configured to invade in the second base and having a physical boundary with the first contactor; and a variance rate in width of the first contactor may be greater than that in width of the second contactor.

In an exemplary embodiment, each of the first liquid metal pattern and the second liquid metal pattern may include conductive particles dispersed therein; and the first contactor and the second contactor may have compositions different from those of the first liquid metal pattern and the second liquid metal pattern.

In an exemplary embodiment, the first liquid metal pattern may include a first contact pad and a first circuit pattern connected to the first contact pad; and the second liquid metal pattern may include a second contact pad overlapping the first contact pad and the contactor, and a second circuit pattern connected to the second contact pad and at least partially overlapping the first circuit pattern.

In an exemplary embodiment, each of the first circuit pattern and the second circuit pattern may have a round shape in plan view.

In an exemplary embodiment, the pattern substrate may further include: a first patterned layer disposed on one surface of the first base; a second patterned layer disposed on one surface of the second base; and a reinforcing layer disposed on a side surface of the first patterned layer.

In an exemplary embodiment, the pattern substrate may further include a transmission blocking layer disposed on the one surface of the first base and configured to be in contact with the first liquid metal pattern; and the transmission blocking layer overlaps the first circuit pattern and does not overlap the first contact pad.

In an exemplary embodiment, the filter element may further comprise: a sealing layer disposed on the one surface of the pattern substrate and having a plurality of holes overlapping the first contact pad; and a plurality of cover members disposed on the plurality of holes of the sealing layer to cover the plurality of holes and configured to be in contact with the first liquid metal pattern, wherein at least a part of the plurality of holes and at least a part of the plurality of cover members may be disposed to not overlap the transmission blocking layer.

In an exemplary embodiment, each of side surfaces of the first contact pad and the first circuit pattern may have an inclination angle of less than 90 degrees; a maximal width of the first contact pad may be greater than that of the first circuit pattern; and an inclination angle of the first circuit pattern may be greater than that of the first contact pad.

According to another exemplary embodiment of the invention, the filter element comprises: a first base; a first passive element disposed on one surface of the first base; a second base disposed on the other surface of the first base and having liquid permeability that is greater than that of the first base; a second passive element disposed on the second base; a first contactor formed by a liquid metal invading in the first base and configured to be electrically connected to the first passive element; and a second contactor formed by a liquid metal invading in the second base and configured to be electrically connected to the first contactor and the second passive element.

In an exemplary embodiment, an average width of the first contactor may be greater than that of the second contactor.

According to an exemplary embodiment of the invention, there is provided a method of preparing a filter element. The method comprises: preparing a first pattern substrate having a first channel formed on one surface thereof and comprising a first base; forming a first liquid metal pattern in the first channel; preparing a second pattern substrate having a second channel formed on one surface thereof and comprising a second base; forming a second liquid metal pattern in the second channel; disposing the other surface of the first pattern substrate to face the other surface of the second pattern substrate; and pressurizing a portion of the first liquid metal pattern to form a contactor invading in the first base and the second base.

In an exemplary embodiment, the pressurization may be performed in a direction from the first pattern substrate to the second pattern substrate; and liquid permeability of the second base may be greater than that of the first base.

In an exemplary embodiment, the method may further comprise, between the preparing of the first pattern substrate and the forming of the first liquid metal pattern, disposing a sealing layer on the one surface of the first pattern substrate; and forming a hole in the sealing layer.

In an exemplary embodiment, the preparing of the first pattern substrate may include: preparing the first base; forming a first patterned layer, which forms the first channel, on the one surface of the first base; forming a reinforcing layer on a side surface of the first patterned layer; forming a transmission blocking layer on the one surface of the first base which is exposed without being covered by the first patterned layer, wherein the forming of the first liquid metal pattern may include injecting a liquid metal through the hole of the sealing layer.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

Figure 1:
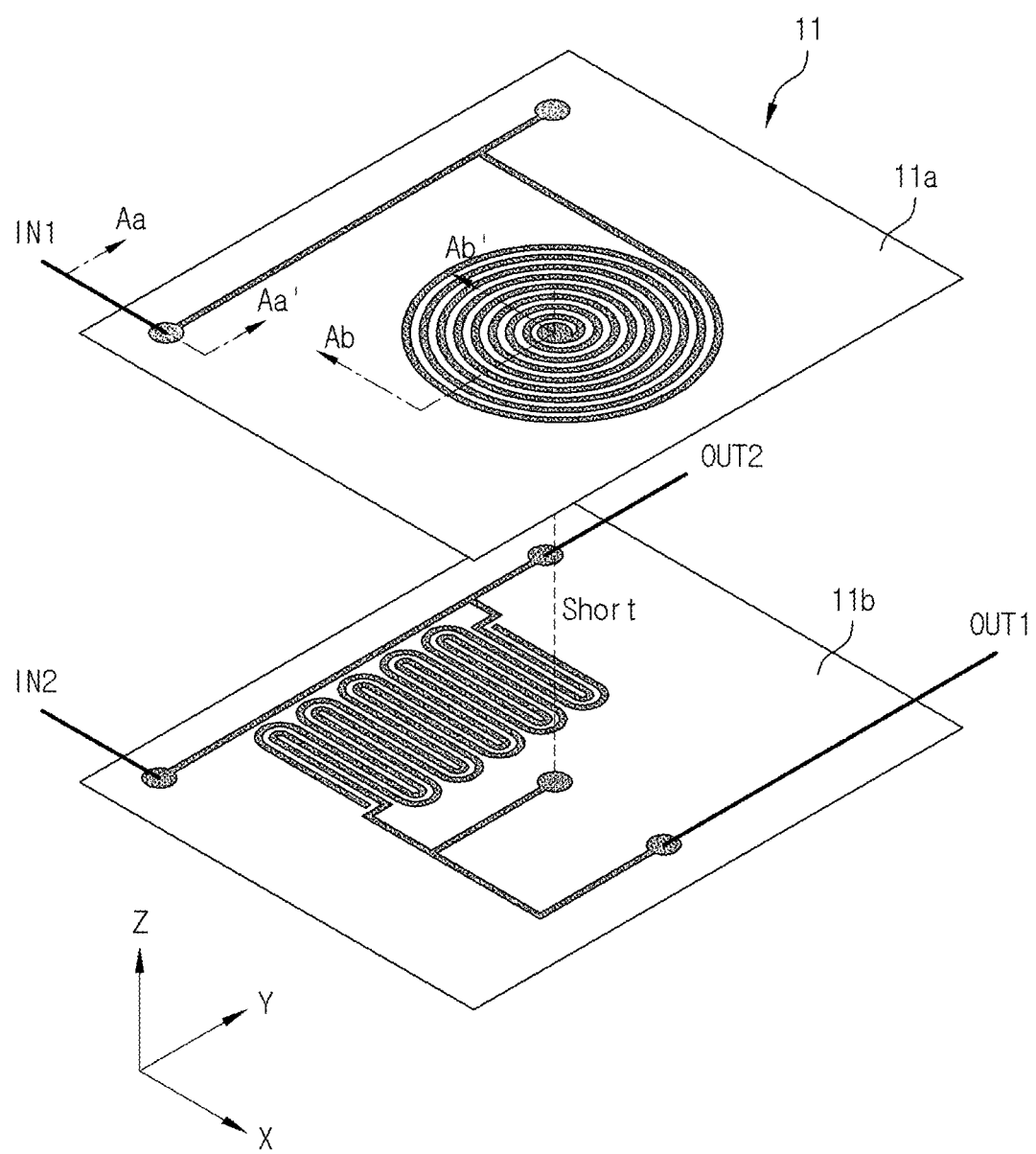
FIG. 1 is an exploded perspective view of a filter element according to one embodiment of the present invention.

Features of the invention and methods of accomplishing the same may be understood more readily by reference to the following detailed description of preferred embodiments and the accompanying drawings. The invention may, however, be embodied in many different forms and should not be construed as being limited to the embodiments set forth herein. Rather, these embodiments are provided so that this disclosure will be thorough and complete and will fully convey the concept of the invention to those skilled in the art, and the invention will only be defined by the appended claims.

It will be understood that when an element or layer is referred to as being "on," "connected to" or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically, electrically and/or fluidly connected to each other.

Like numbers refer to like elements throughout. As used herein, the term "and/or" includes any and all combinations of one or more of the associated listed items.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Spatially relative terms, such as "below," "lower," "under," "above," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an" and "the" are intended to include the plural forms as well, including "at least one," unless the context clearly indicates otherwise. It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof. "At least one" is not to be construed as limiting "a" or "an." "Or" means "and/or." As used herein, the term "and/or" includes any and all combinations of one or more of the associated listed items.

In this disclosure, a first direction X means any direction in a plane, and a second direction Y means another direction intersecting the first direction X in the plane. A third direction Z means a direction perpendicular to the plane. Unless otherwise defined, the term "plane" refers to a plane to which the first direction X and the second direction Y belong. Further, unless otherwise defined, the term "overlapping" means overlapping in the third direction Z in plan view.

Hereinafter, the present invention will be described in detail with reference to the accompanying drawings.

Figure 2:
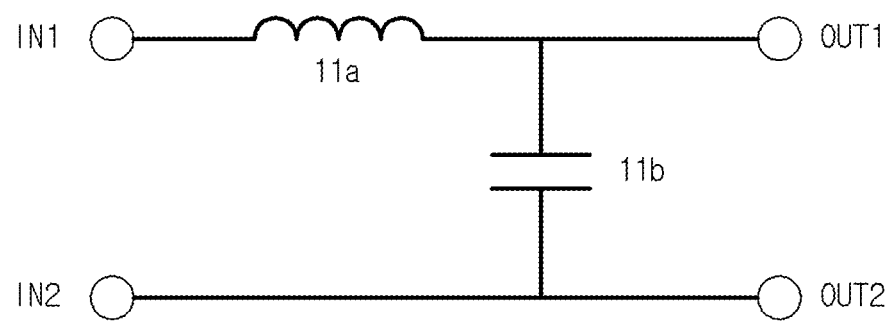
FIG. 2 is a diagram illustrating an equivalent circuit of the filter element of FIG. 1.
Figure 3:
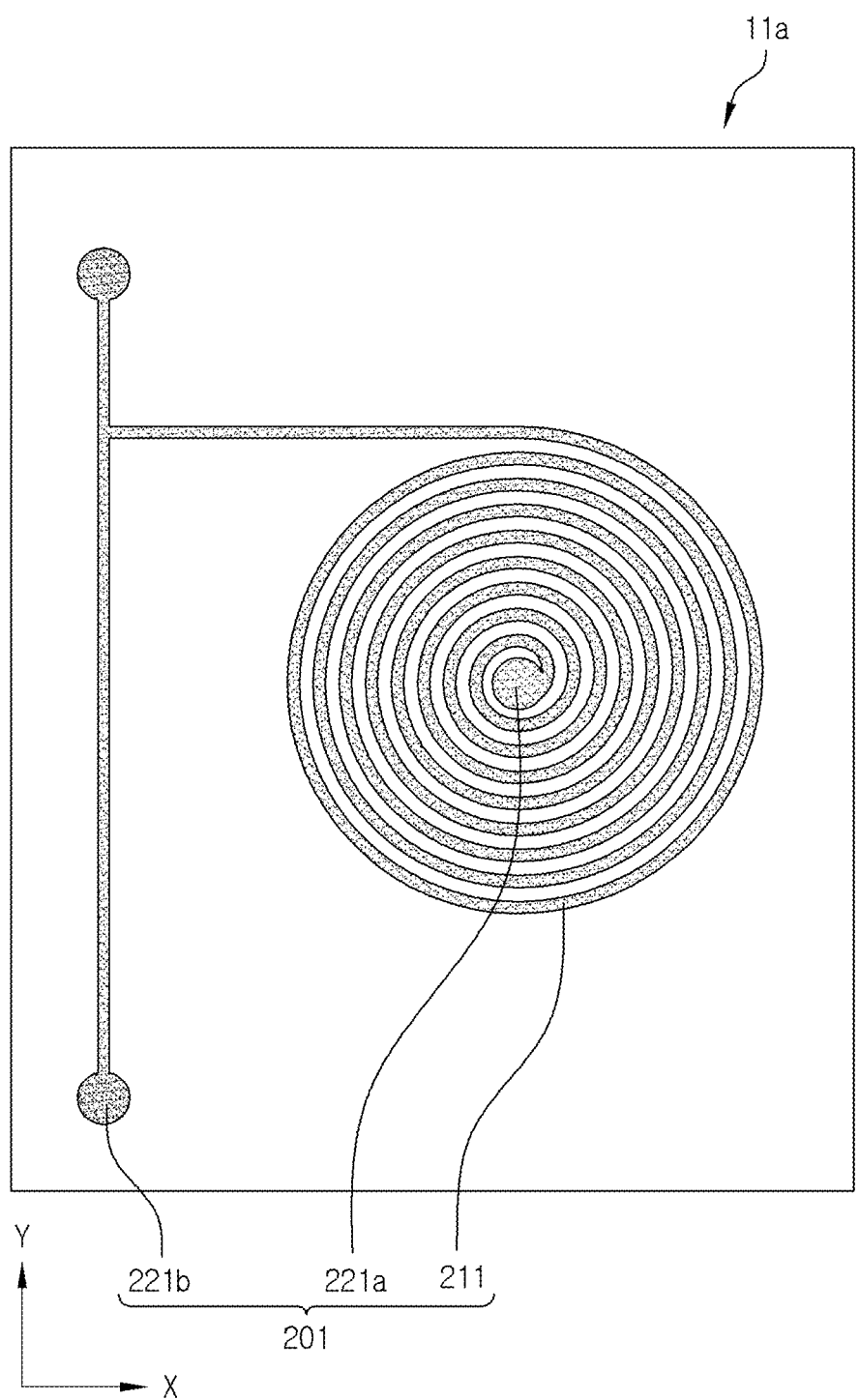
FIG. 3 is a plan view of an inductor element of FIG. 1.
Figure 4:
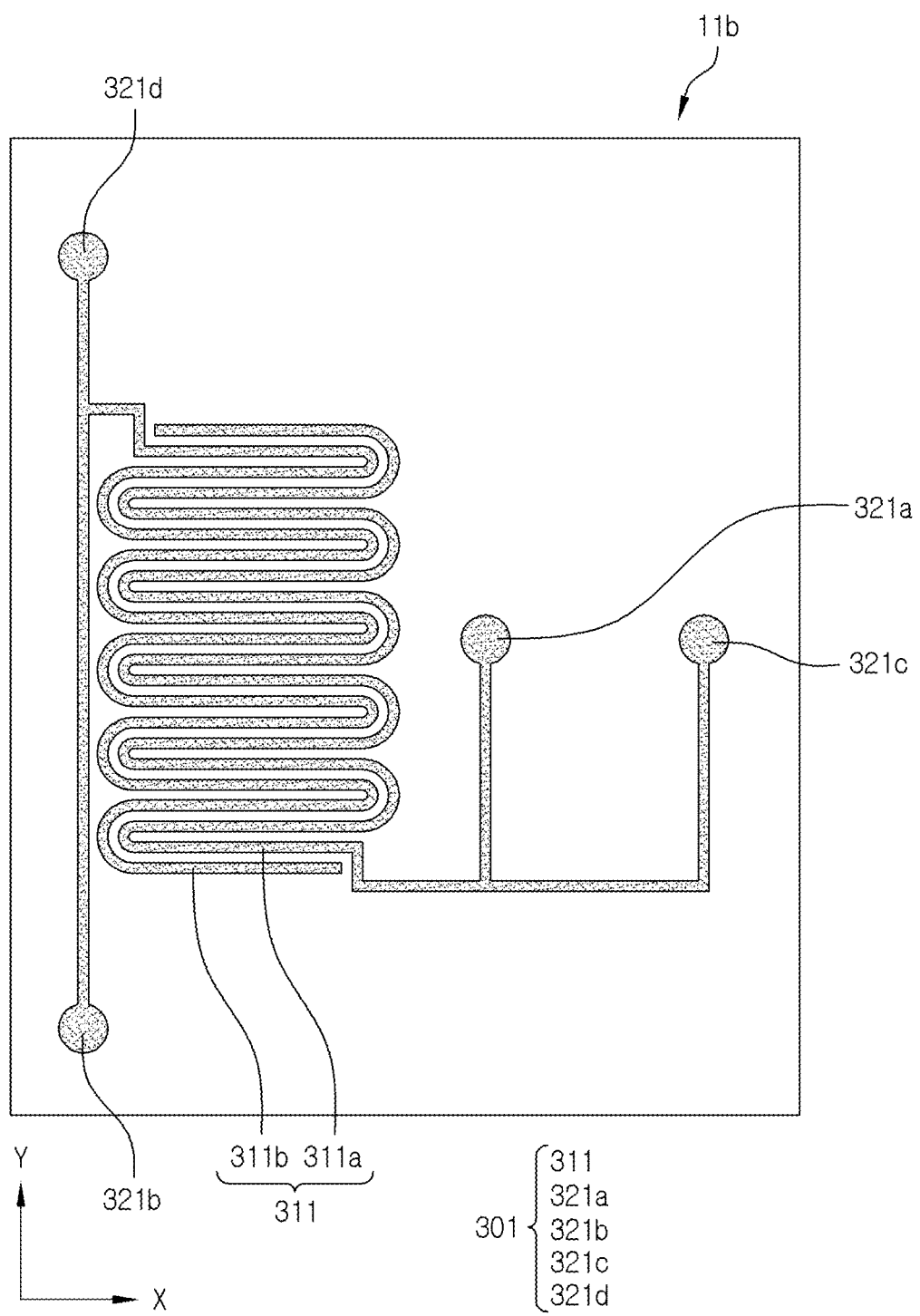
FIG. 4 is a plan view of a capacitor element of FIG. 1.

FIG. 1 is an exploded perspective view of a filter element 11 according to one embodiment of the present invention. FIG. 2 is a diagram illustrating an equivalent circuit of the filter element 11 of FIG. 1. FIG. 3 is a plan view of an inductor element 11a of FIG. 1. FIG. 4 is a plan view of a capacitor element 11b of FIG. 1.

Referring to FIGS. 1 to 4, the filter element 11 according to the present embodiment includes the inductor element 11a and the capacitor element 11*b* which are electrically connected to each other. The filter element 11 may be a low-pass filter in which a first input terminal IN1 is connected to the inductor element 11*a*, and a second input terminal IN2, a first output terminal OUT1, and a second output terminal OUT2 are connected to the capacitor element 11*b*.

When a current flows in the inductor element 11*a*, the inductor element 11*a* may be configured to generate an induced electromotive force. In an exemplary example, the inductor element 11*a* may be implemented through a first liquid metal pattern 201. The first liquid metal pattern 201 may include an inductor circuit pattern 211 and, connected to the inductor circuit pattern 211, a first inductor contact pad 221*a* and a second inductor contact pad 221*b*.

In plan view, the inductor circuit pattern 211 may have a spiral shape. Specifically, the inductor circuit pattern 211 may have a spiral shape of which distance from a spiral center increases. The inductor circuit pattern 211, which will be described below, may be formed using a liquid metal. When a current flows in the inductor circuit pattern 211, an induced electromotive force may be generated in a spiral-shaped or annular-shaped line such that the inductor circuit pattern 211 may serve as an inductor.

Further, in plan view, the inductor circuit pattern 211 is formed as a rounded line instead of an angled line so that formation of the inductor circuit pattern 211 using a liquid metal may be facilitated. As described below, the inductor circuit pattern 211 may be formed by injecting a liquid metal into a channel. For example, when the inductor circuit pattern 211 has a round shape as in the present embodiment as compared with a case of having an angled shape, injection of the liquid metal may be facilitated and an increase of a pressure inside the channel may be suppressed such that a larger amount of liquid metal may be injected. Further, in plan view, when the inductor circuit pattern 211 is formed as an angled line, a pressure inside the channel increases and thus an unfilled region may occur in the vicinity of an edge, or an unfilled region occurs in the middle of a line to cause an increase in line resistance or a defect in which a line becomes an open circuit.

The first inductor contact pad 221*a* may be located on one end portion of the inductor circuit pattern 211 forming the line, and the second inductor contact pad 221*b* may be located on the other end portion of the inductor circuit pattern 211. Each of the first inductor contact pad 221*a* and the second inductor contact pad 221*b* may extend as compared with a line width of the inductor circuit pattern 211, thereby having an advantageous structure for an electrical connection. That is, a maximal width of each of the first inductor contact pad 221*a* and the second inductor contact pad 221*b* may be greater than a maximal width of the inductor circuit pattern 211. The first inductor contact pad 221*a* and/or the second inductor contact pad 221*b* may be connected to other components of the filter element 11 and other elements or electrical lines outside the filter element 11.

The first inductor contact pad 221*a* may be located at substantially a center of the spiral-shaped inductor circuit pattern 211. The first inductor contact pad 221*a* may be electrically connected to the capacitor element 11*b*, which will be described below, to form a short-circuit node. Further, the first inductor contact pad 221*a* may be electrically equivalent to the first output terminal OUT1 of the filter element 11, but the present invention is not limited thereto.

Furthermore, the second inductor contact pad 221*b* may be located outside the spiral-shaped inductor circuit pattern 211. The second inductor contact pad 221*b* may be electrically equivalent to the first input terminal IN1 of the filter element 11. One or more second inductor contact pads 221*b* may be provided, but the present invention is not limited thereto.

Further, the capacitor element 11*b* may be configured to accumulate electrified charges using an electrostatic induction phenomenon. In an exemplary example, the capacitor element 11*b* may be implemented through a second liquid metal pattern 301. The second liquid metal pattern 301 may include a capacitor circuit pattern 311 and, connected to the capacitor circuit pattern 311, a first capacitor contact pad 321*a* and a second capacitor contact pad 321*b*.

In plan view, the capacitor circuit pattern 311 may include two line patterns spaced apart from each other. For example, the capacitor circuit pattern 311 may include a first capacitor circuit pattern 311*a* and a second capacitor circuit pattern 311*b* which are spaced from each other. The first capacitor circuit pattern 311*a* and the second capacitor circuit pattern 311*b* may form one side and the other side terminal of the capacitor element 11*b*, respectively.

The first capacitor circuit pattern 311*a* and the second capacitor circuit pattern 311*b* may each have a substantial "S" shape and may be in a state of being spaced at a regular interval apart from each other. Consequently, an area of a facing surface between the first capacitor circuit pattern 311*a* and the second capacitor circuit pattern 311*b* may increase and a capacitor characteristic may be improved.

Further, in plan view, the capacitor circuit pattern 311 is formed in an "S"-shaped round line instead of an angled line so that formation of the capacitor circuit pattern 311 using a liquid metal may be facilitated. As described below, the capacitor circuit pattern 311 may be formed by injecting a liquid metal into a channel. For example, when the capacitor circuit pattern 311 has the round shape as in the present embodiment as compared with a case of having an angled shape, injection of the liquid metal may be facilitated and an increase of a pressure inside the channel may be suppressed such that a larger amount of liquid metal may be injected. Further, in plan view, when the capacitor circuit pattern 311 is formed as an angled line, a pressure inside the channel increases and thus an unfilled region may occur in the vicinity of an edge, or an unfilled region occurs in the middle of a line to cause an increase in line resistance or a defect in which a line becomes an open circuit.

The first capacitor contact pad 321*a* may be located on one end of the first capacitor circuit pattern 311*a* forming the line, and the second capacitor contact pad 321*b* may be located on one end portion of the second capacitor circuit pattern 311*b*. Each of the first capacitor contact pad 321*a* and the second capacitor contact pad 321*b* may extend as compared with a line width of the capacitor circuit pattern 311, thereby having an advantageous structure for an electrical connection. That is, a maximal width of each of the first capacitor contact pad 321*a* and the second capacitor contact pad 321*b* may be greater than a maximal width of the capacitor circuit pattern 311. The first capacitor contact pad 321*a* and/or the second capacitor contact pad 321*b* may be connected to other components of the filter element 11 and other elements or electrical lines outside the filter element 11.

In some examples, the second liquid metal pattern 301 may further include a third capacitor contact pad 321*c* and a fourth capacitor contact pad 321*d*. The third capacitor contact pad 321*c* may be electrically equivalent to the first capacitor contact pad 321*a*, and the fourth capacitor contact pad 321*d* may be electrically equivalent to the second capacitor contact pad 321*b*.

The first capacitor contact pad 321*a* may be electrically connected to the above-described inductor element 11*a* to form a short-circuit node. Further, the first capacitor contact pad 321*a* may be electrically connected to the third capacitor contact pad 321*c*. The first capacitor contact pad 321*a* and the third capacitor contact pad 321*c* may each be electrically equivalent to the first output terminal OUT1 of the filter element 11, but the present invention is not limited thereto.

Further, the second capacitor contact pad 321*b* may be electrically equivalent to the second input terminal IN2 of the filter element 11. Further, the second capacitor contact pad 321*b* may be electrically connected to the fourth capacitor contact pad 321*d*. The fourth capacitor contact pad 321*d* may be electrically equivalent to the second output terminal OUT2, but the present invention is not limited thereto.

Further, FIG. 4 illustrates a case in which the first capacitor contact pad 321*a* and the third capacitor contact pad 321*c* are spaced apart in the first direction X, and the second capacitor contact pad 321*b* and the fourth capacitor contact pad 321*d* are spaced in the second direction Y, but the present invention is not limited thereto.

Figure 5:
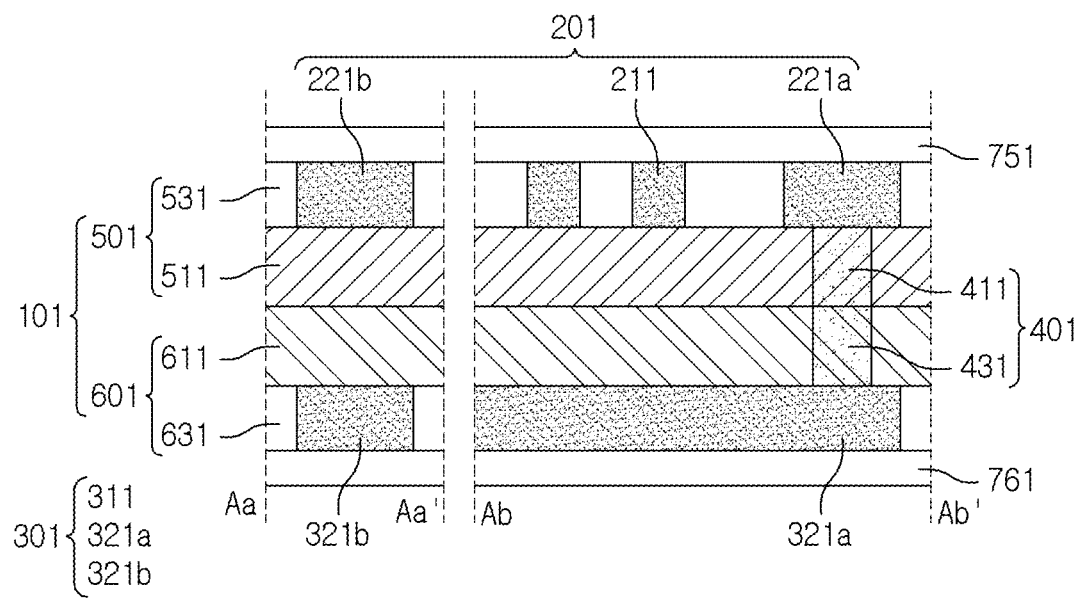
FIG. 5 shows comparative cross-sectional views taken along lines Aa-Aa' and Ab-Ab' of FIG. 1.

Hereinafter, the filter element 11 according to the present embodiment will be described in more detail with reference to FIG. 5. FIG. 5 shows comparative cross-sectional views taken along lines Aa-Aa' and Ab-Ab' of FIG. 1. Specifically, a left diagram of FIG. 5 is a cross-sectional view illustrating the vicinity of the second inductor contact pad 221*b* and the second capacitor contact pad 321*b*. Further, a right diagram of FIG. 5 is a cross-sectional view illustrating the vicinity of the first inductor contact pad 221*a* and the first capacitor contact pad 321*a*.

More referring to FIG. 5, the filter element 11 according to the present embodiment may include a pattern substrate 101, the first liquid metal pattern 201 disposed on one surface of the pattern substrate 101 (an upper surface based on FIG. 5), the second liquid metal pattern 301 disposed on the other surface of the pattern substrate 101 (a lower surface based on FIG. 5), and a contactor 401 for conducting the first liquid metal pattern 201 and the second liquid metal pattern 301 and may further include a first sealing layer 751 and a second sealing layer 761.

One surface and the other surface of the pattern substrate 101 may each have a patterned structure. For example, one surface of the pattern substrate 101 may have a first channel or a first trench, and the other surface of the pattern substrate 101 may have a second channel or a second trench.

In an exemplary example, the pattern substrate 101 may include a first pattern substrate 501 and a second pattern substrate 601. One surface (a lower surface) of the first pattern substrate 501 and one surface (an upper surface) of the second pattern substrate 601 may be disposed to face each other or be bonded to each other. In some examples, a bonding layer (not shown) may be disposed between the first pattern substrate 501 and the second pattern substrate 601.

The first pattern substrate 501 may include a first base 511 and a first patterned layer 531 disposed on the first base 511. The first base 511 may be made of a flexible material having flexibility and/or stretchability. For example, the first base 511 may be made of paper or a polymeric resin such as polydimethylsiloxane or polyimide. Further, the first base 511 may have fine pores therein. Alternatively, the first base 511 may be made of a glass material or the like.

The first patterned layer 531 may form a first channel filled with the first liquid metal pattern 201. That is, in plan view, the first patterned layer 531 may have a reversed pattern of the first liquid metal pattern 201. An upper surface of the first base 511 not covered with the first patterned layer 531 may be exposed. The first patterned layer 531 may have an insulating property. For example, the first patterned layer 531 may include a polymer material such as polyethylene terephthalate, polymethylmethacrylate, polycarbonate, or the like but the present invention is not limited thereto. Further, the first patterned layer 531 may have hydrophobicity that is greater than that of the first base 511.

As described above, the inductor element 11*a* may be implemented by the first liquid metal pattern 201. Further, the first liquid metal pattern 201 may include the inductor circuit pattern 211, the first inductor contact pad 221*a*, and the second inductor contact pad 221*b* with which the first channel of the first pattern substrate 501 is filled. The first liquid metal pattern 201 may include a liquid metal maintaining a liquid phase at room temperature. The liquid metal may include gallium and indium, but the present invention is not limited thereto. The first liquid metal pattern 201 may be in contact with the first base 511.

The first sealing layer 751 may be disposed on the first liquid metal pattern 201. The first sealing layer 751 may have an insulating property and seal the first liquid metal pattern 201. The first sealing layer 751 may be made of the same material as or a material different from that of the first patterned layer 531. Further, the first sealing layer 751 may have hydrophobicity that is greater than that of the first base 511.

Similarly, the second pattern substrate 601 may include a second base 611 and a second patterned layer 631 disposed on the second base 611. The second base 611 may be made of a flexible material having flexibility and/or stretchability. For example, the second base 611 may be made of paper or a polymeric resin such as polydimethylsiloxane or polyimide. Further, the second base 611 may have fine pores therein.

In an exemplary example, the second base 611 may be formed of a material different from that of the first base 511. Specifically, the second base 611 may be made of a material having liquid permeability that is greater than that of the first base 511. When the first liquid metal pattern 201 located on an upper side forms the inductor element 11*a* and the second liquid metal pattern 301 located on a lower side forms the capacitor element 11*b* based on the first base 511 and the second base 611, the second base 611 is configured to have greater liquid permeability such that a contact area between the contactor 401 and the second liquid metal pattern 301 may increase to improve electrical stability. This will be described in detail below with a method of manufacturing the filter element.

The second patterned layer 631 may form a second channel filled with the second liquid metal pattern 301. That is, in plan view, the second patterned layer 631 may have a reversed pattern of the second liquid metal pattern 301. A lower surface of the second base 611 not covered with the second patterned layer 631 may be exposed. The second patterned layer 631 may be made of the same material as or a material different from that of the first patterned layer 531. Further, the second patterned layer 631 may have hydrophobicity that is greater than that of the second patterned layer 631.

As described above, the capacitor element 11*b* may be implemented by the second liquid metal pattern 301. Further, the second liquid metal pattern 301 may include the capacitor circuit pattern 311 (which is not shown in the cross-sectional view) with which the second channel of the second pattern substrate 601 is filled, the first capacitor contact pad 321*a*, and the second capacitor contact pad 321*b* and may further include the third capacitor contact pad 321*c*

(which is not shown in the cross-sectional view) and the fourth capacitor contact pad 321*d* (which is not shown in the cross-sectional view). The first capacitor contact pad 321*a* may overlap the first inductor contact pad 221*a* in the third direction Z, and the second capacitor contact pad 321*b* may overlap the second inductor contact pad 221*b* in the third direction Z. Further, the capacitor circuit pattern 311 may at least partially overlap the inductor circuit pattern 211 in the third direction Z.

The second liquid metal pattern 301 may include the same liquid metal as or a liquid metal different from that of the first liquid metal pattern 201. The liquid metal may include gallium and indium, but the present invention is not limited thereto. The second liquid metal pattern 301 may be in contact with the second base 611.

The second sealing layer 761 may be disposed on the second liquid metal pattern 301. The second sealing layer 761 may have an insulating property and seal the second liquid metal pattern 301. The second sealing layer 761 may be made of the same material as or a material different from that of the second patterned layer 631. The second sealing layer 761 may have hydrophobicity that is greater than that of the second base 611.

The contactor 401 may electrically connect the first liquid metal pattern 201 to the second liquid metal pattern 301 and, specifically, connect the first inductor contact pad 221*a* to the first capacitor contact pad 321*a*. The contactor 401, the first inductor contact pad 221*a*, and the second capacitor contact pad 321*b* may form an electrical equivalent to the first output terminal OUT1 of the filter element 11.

The contactor 401 may be a portion by which the pattern substrate 101 is at least partially invaded by a liquid metal which is the same as the first liquid metal pattern 201 and the second liquid metal pattern 301. That is, the contactor 401 refers to a portion by which the liquid metal invades in the first base 511 and the second base 611 and is distinguished from other portions of the first base 511 and the second base 611, which are not invaded by the liquid metal. The planar shape of the contactor 401 may be substantially formed as a circular or polygonal shape, but the present invention is not limited thereto.

In an exemplary example, the contactor 401 may include a first contactor 411 invading in the first base 511 and a second contactor 431 invading in the second base 611. That is, the first contactor 411 is formed by which the liquid metal invades in the first base 511, and the second contactor 431 may be formed by which the liquid metal invades in the second base 611. The first contactor 411 may be electrically connected to the first liquid metal pattern 201, and second contactor 431 may be electrically connected to the first contactor 411 and the second liquid metal pattern 301.

Consequently, even though the contactor 401 is formed, a physical boundary may be present between the first base 511 and the second base 611. Accordingly, a physical boundary may also be present between the first contactor 411 and the second contactor 431. Further, physical boundaries may be present between the first contactor 411 and the first liquid metal pattern 201 and between the second contactor 431 and the second liquid metal pattern 301.

The filter element 11 according to the present embodiment may have excellent flexibility and stretchability by forming passive elements constituting the filter element 11, e.g., by forming lines of the inductor element 11*a* and the capacitor element 11*b*, using a liquid metal which maintains a liquid state at room temperature. Further, even when the filter element 11 is completely folded, it is possible to prevent a problem wherein the lines are damaged or cracks occur on the lines.

Further, the filter element 11 includes the contactor 401 invading in the first base 511 and the second base 611, which have liquid permeability, without forming a via hole for an electrical connection such that a manufacturing cost may be reduced and a process may be simplified.

For example, when a pressure is applied from the first base 511 to the second base 611 in the process of forming the contactor 401, the liquid permeability of the second base 611 having a relatively long liquid penetration distance is made greater than the liquid permeability of the first base 511 such that an invasion degree of the liquid metal in the first contactor 411 and the second contactor 431 may be maintained to be substantially uniform and an electrical connection between the upper inductor element 11*a* and the lower capacitor element 11*b* may be improved.

Hereinafter, filter elements according to other embodiments of the present invention will be described. However, a duplicate description of a configuration substantially identical or similar to that of the filter element 11 according to the above-described embodiment will be omitted, and this will be apparently understood to those skilled in the art to which the present invention pertains from the accompanying drawings. The same reference numerals are assigned to the same components.

Figure 6:
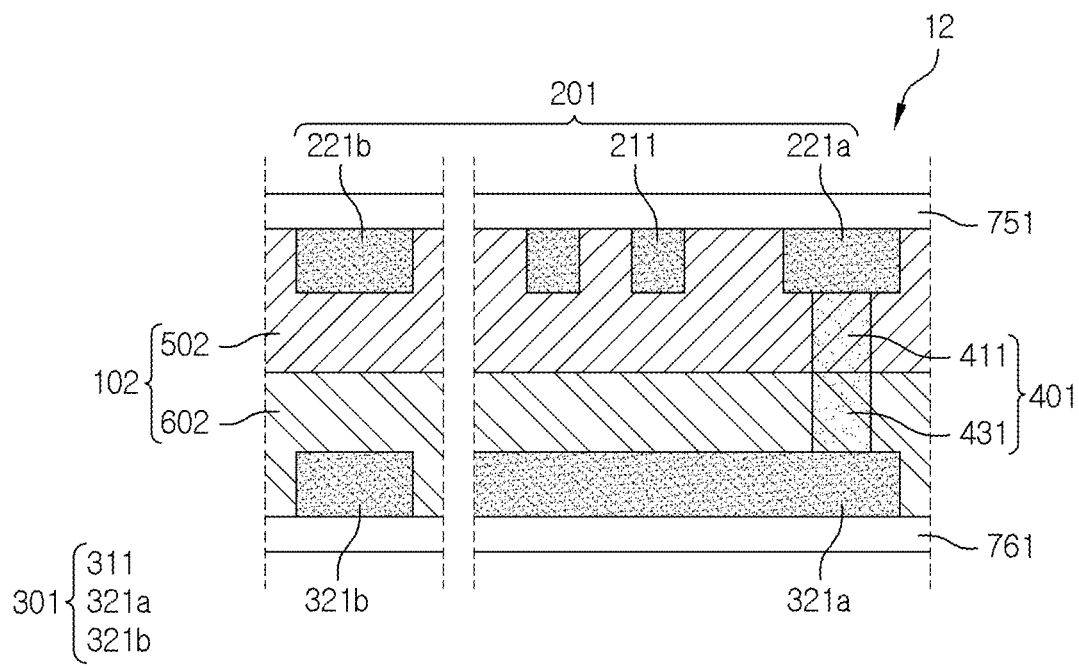
FIG. 6 shows cross-sectional views illustrating a filter element according to another embodiment of the present invention.

FIG. 6 shows cross-sectional views of a filter element 12 according to another embodiment of the present invention which is a comparative cross-sectional view illustrating a position corresponding to that of FIG. 5.

Referring to FIG. 6, the filter element 12 according to the present embodiment includes a pattern substrate 102 and the first liquid metal pattern 201 and the second liquid metal pattern 301 which are disposed on one surface and the other surface of the pattern substrate 102, respectively. There is a difference from the filter element 11 according to the embodiment shown in FIG. 5 in that one surface of a first pattern substrate 502 (an upper surface based on FIG. 6) has a patterned structure to form a first channel, and one surface of a second pattern substrate 602 (a lower surface based on FIG. 6) has a patterned structure to form a second channel.

The first pattern substrate 502 may itself form a base. Similarly, the second pattern substrate 602 may itself form a base. The first pattern substrate 502 and the second base 602 may be made of paper or a polymeric resin such as polydimethylsiloxane or polyimide. Further, a protruding pattern of the first pattern substrate 502 forming the first channel and a protruding pattern of the second pattern substrate 602 forming the second channel may have hydrophobicity that is less than those of the first sealing layer 751 and the second sealing layer 761, respectively.

Consequently, the liquid metals forming the first liquid metal pattern 201 and the second liquid metal pattern 301 may partially penetrate into side surfaces of the protruding patterns. The filter element 12 according to the present embodiment has an effect of omitting an operation of forming a separate pattern layer on the base.

Figure 7:
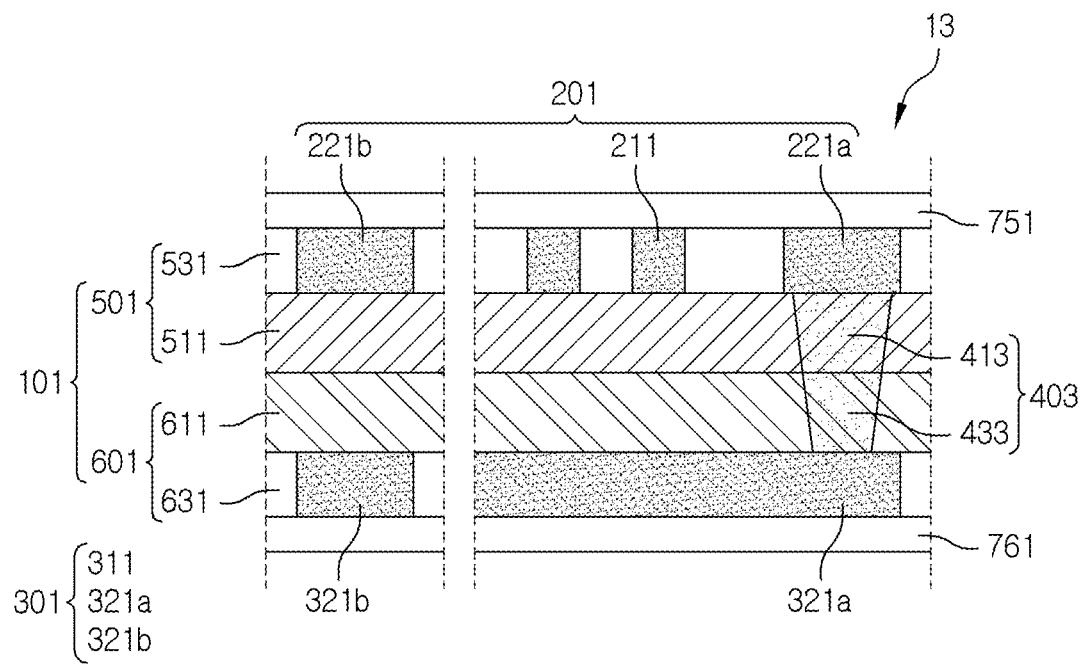
FIG. 7 shows cross-sectional views illustrating a filter element according to still another embodiment of the present invention.

FIG. 7 shows cross-sectional views of a filter element 13 according to still another embodiment of the present invention which is a comparative cross-sectional view illustrating a position corresponding to that of FIG. 5.

Referring to FIG. 7, there is a difference from the filter element 11 according to the embodiment shown in FIG. 5 in that a width of a contactor 403 of the filter element 13 according to the present embodiment is varied.

The width of the contactor 403 may decrease in a direction from the first liquid metal pattern 201 toward the second liquid metal pattern 301. When a shape of a portion in which the contactor 403 is in contact with the first liquid metal pattern 201 is substantially identical to a shape of a portion in which the contactor 403 is in contact with the second liquid metal pattern 301, a contact area between the contactor 403 and the first liquid metal pattern 201 may be greater than a contact area between the contactor 403 and the second liquid metal pattern 301. Further, an average width of a first contactor 413 may be greater than that of a second contactor 433.

In an exemplary example, when the filter element 13 is a low-pass filter element, the portion at which the contactor 403 is in contact with the first liquid metal pattern 201 is electrically equivalent to an output terminal of the low-pass filter element (e.g., a first output terminal), the first liquid metal pattern 201 constitutes an inductor element, and the second liquid metal pattern 301 constitutes a capacitor element, the width of the contactor 403 may decrease in the direction from the first liquid metal pattern 201 toward the second liquid metal pattern 301.

A contact area between the first contactor 413 and the second contactor 433 may be greater than a contact area between the second contactor 433 and the second liquid metal pattern 301 and a contact area between the first contactor 413 and the first liquid metal pattern 201. In some examples, a decrease rate in width of the first contactor 413 may be substantially equal to that in width of the second contactor 433.

Although the present invention is not limited thereto, when a high load is applied to any output terminal of the filter element 13 and, specifically, when a high load is applied to a node shared by the inductor element and the capacitor element, the contact area between the first liquid metal pattern 201 and the contactor 403 is maximized as in the present embodiment such that there is an effect which is capable of reducing load resistance.

Figure 8:
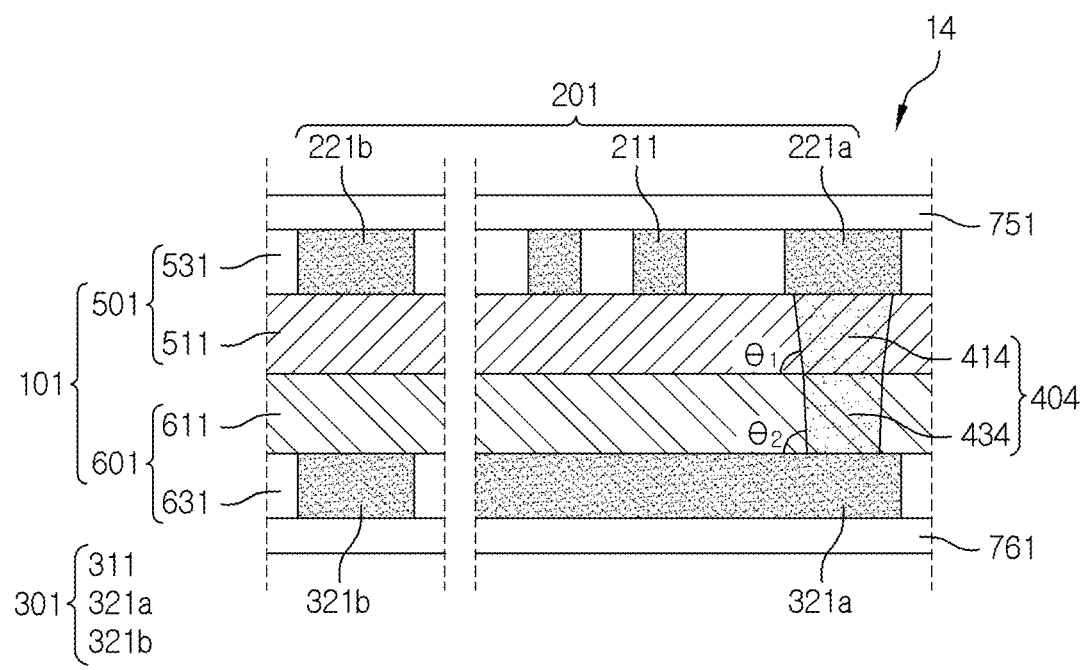
FIGS. 8 to 11 show cross-sectional views illustrating a filter element according to still another embodiment of the present invention.

FIG. 8 shows cross-sectional views of a filter element 14 according to still another embodiment of the present invention which is a comparative cross-sectional view illustrating a position corresponding to that of FIG. 5.

Referring to FIG. 8, there is a difference in that variance rates in width of a first contactor 414 and a second contactor 434 of the filter element 14 according to the present embodiment is different from a variance rate in width of the filter element 13 according to the embodiment shown in FIG. 7.

In an exemplary example, when the filter element 14 is a low-pass filter element, a portion in which a contactor 404 is in contact with the first liquid metal pattern 201 is electrically equivalent to an output terminal of the low-pass filter element (e.g., a first output terminal), the first liquid metal pattern 201 constitutes an inductor element, and the second liquid metal pattern 301 constitutes a capacitor element, a width of the first contactor 414 may decrease in the direction from the first liquid metal pattern 201 toward the second liquid metal pattern 301. Further, a width of the contactor 434 may decrease in the direction from the first liquid metal pattern 201 toward the second liquid metal pattern 301 or may not be varied.

That is, a decrease rate in width of the first contactor 414 may be greater than a decrease rate in width of the second contactor 434. In this disclosure, the term "variance rate in width" refers to a ratio of a length in a width direction (i.e., the first direction X and/or the second direction Y) to a length in a height direction (i.e., the third direction Z).

Consequently, a first inclined angle $\theta_1$ formed by the first base 511 surrounding the first contactor 414 may be smaller than a second inclined angle $\theta_2$ formed by the second base 611 surrounding the second contactor 434. Alternatively, the variance rate in width of the second contactor 434 may be substantially zero. A difference between the decrease rates in width of the first contactor 414 and the second contactor 434 may be due to a difference in liquid permeability difference between the first base 511 and the second base 611, but the present invention is not limited thereto.

A width of the contactor 404 of the filter element 14 according to the present embodiment entirely decreases from an upper side to a lower side. However, a decrease in width of the second contactor 434 in contact with the second liquid metal pattern 301 is minimized such that a contact area between the second liquid metal pattern 301 and the second contactor 434 may increase. Thus, there is an effect in that an increase of contact resistance may be prevented, and an electrical connection between the upper inductor element and the lower capacitor element may be improved.

Figure 9:
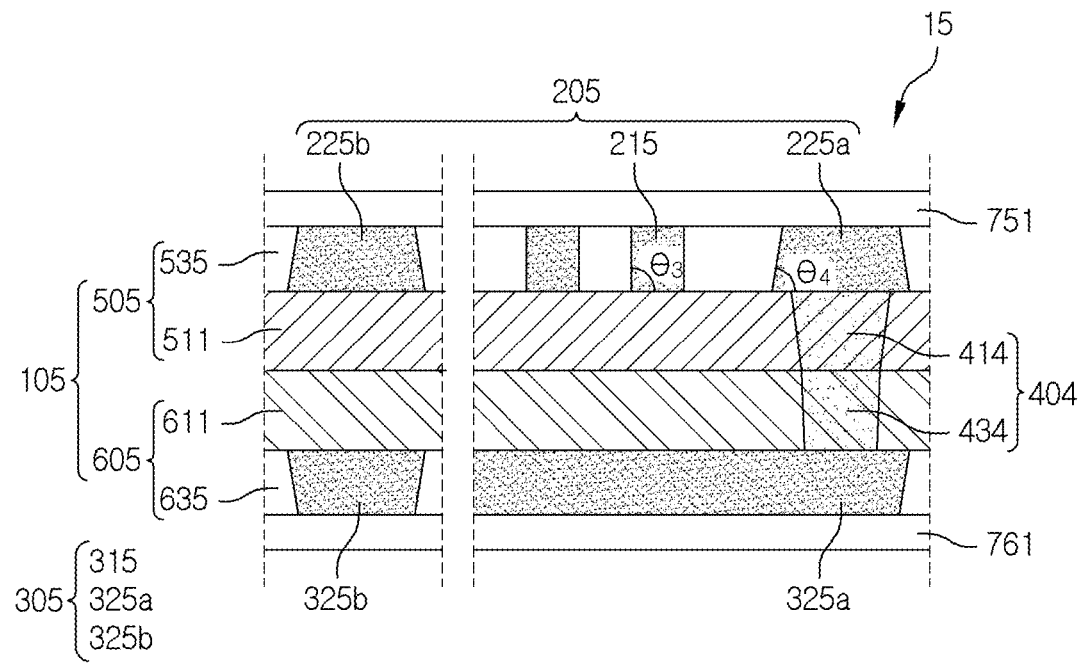

FIG. 9 shows cross-sectional views illustrating a filter element 15 according to still another embodiment of the present invention which is a comparative cross-sectional view illustrating a position corresponding to that of FIG. 5.

Referring to FIG. 9, there is a difference from the filter element 11 according to the embodiments shown in FIG. 5 in that a liquid metal pattern of the filter element 15 according to the present embodiment has a partially tapered shape.

In exemplary example, each side surface of a first inductor contact pad 225a and a second inductor contact pad 225b of a first liquid metal pattern 205 may be inclined. On the other hand, a side surface of an inductor circuit pattern 215 of the first liquid metal pattern 205 may not be inclined substantially. That is, a third inclined angle $\theta_3$ is substantially 90 degrees. The third inclined angle $\theta_3$ may be larger than a fourth inclined angle $\theta_4$.

Similarly, each side surface of a first capacitor contact pad 325a and a second capacitor contact pad 325b of the second liquid metal pattern 305 may be inclined. Meanwhile, although not shown in the cross-sectional views, a side surface of a capacitor circuit pattern 315 (including a first capacitor circuit pattern portion and a second capacitor circuit pattern portion) of a second liquid metal pattern 305 may not be substantially inclined.

Meanwhile, each of an inner wall of a first patterned layer 535 disposed on the first base 511 and an inner wall of a channel of a second patterned layer 635 disposed on the second base 611 may be inclined partially and inversely. A liquid metal line forming an inductor element and a capacitor element of the filter element 15 according to the present embodiment may have a partially tapered shape. Consequently, it is possible to stably trap the liquid metal maintaining a liquid state at room temperature. In particular, the contact pads 225a, 225b, 325a, and 325b which each occupy a relatively large area as compared with the line, may be portions at which an electrical connection is made between the inductor element and the capacitor element or at which an electrical connection with an external other element is made, and electrical connection characteristics in the contact pads 225a, 225b, 325a, and 325b may be improved.

Meanwhile, as described with reference to FIG. 8, the first contactor 414 and the second contactor 434 have different decrease rates in width.

Figure 10:
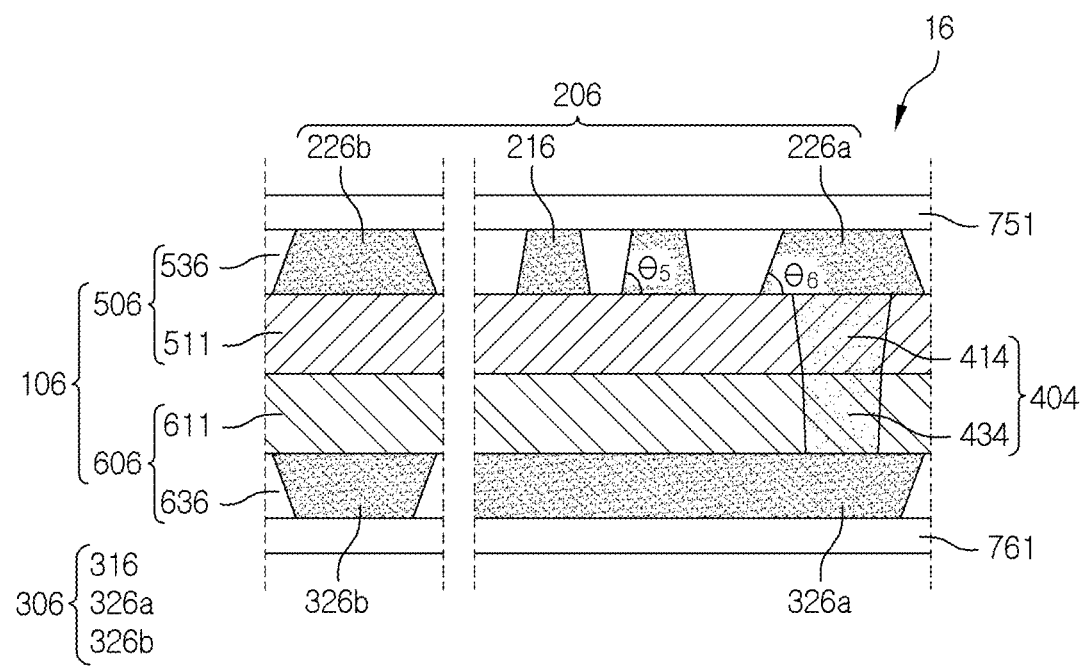

FIG. 10 shows cross-sectional views illustrating a filter element 16 according to still another embodiment of the present invention which is a comparative cross-sectional view illustrating a position corresponding to that of FIG. 5.

Referring to FIG. 10, there is a difference between the filter element 16 according to the present embodiment and the filter element 15 according to the embodiment of FIG. 9 in that a side surface of an inductor circuit pattern 216 of a first liquid metal pattern 206 is inclined less than 90 degrees, and a side surface of a capacitor circuit pattern 316 of a second liquid metal pattern 306 is inclined less than 90 degrees.

In an exemplary example, all of the side surfaces of the inductor circuit pattern 216, a first inductor contact pad 226a, and a second inductor contact pad 226b of the first liquid metal pattern 206 may be inclined. Similarly, all of the side surfaces of the capacitor circuit pattern 316, a first capacitor contact pad 326a, and a second capacitor contact pad 326b of the second liquid metal pattern 306 may be inclined. In some examples, a fifth inclined angle $\theta_5$ of the side surface of the inductor circuit pattern 216 may be larger than a sixth inclined angle $\theta_6$ of the side surface of the first inductor contact pad 226a.

Meanwhile, an inner wall of a first patterned layer 536 disposed on the first base 511 and an inner wall of a channel of a second patterned layer 636 disposed on the second base 611 may each be inclined partially and inversely. A liquid metal line of the filter element 16 according to the present embodiment may have a tapered shape, thereby stably trapping the liquid metal. Although the present invention is not limited thereto, when the inclination of the liquid metal line is excessively large, sheet resistance in upper and lower portions of the liquid metal line may be locally differentiated.

Therefore, the inductor circuit pattern 216 and the capacitor circuit pattern 316, which significantly contribute to a current flow, may each be inclined within a range not causing non-uniformity of the sheet resistance, thereby stably trapping the liquid metal. Further, the inductor contact pads 226a and 226b and the capacitor contact pads 326a and 326b, which contribute to the electrical connection rather than the current flow, may each be formed to be inclined sufficiently such that there is an effect of improving the electrical connection. For example, the fifth inclined angle $\theta_5$ may be in a range of about 80 degrees to about 85 degrees, and the sixth inclined $\theta6$ may be in a range of about 60 degrees to about 84 degrees.

Figure 11:
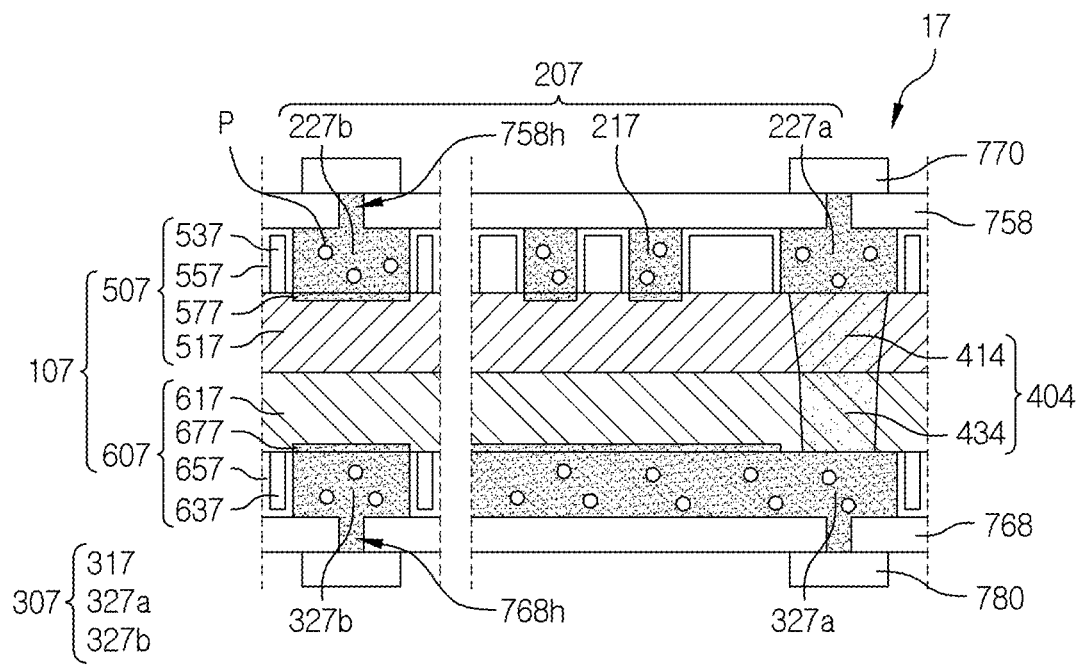

FIG. 11 shows cross-sectional views illustrating a filter element 17 according to still another embodiment of the present invention which is a comparative cross-sectional view illustrating a position corresponding to that of FIG. 5.

Referring to FIG. 11, there is a difference from the filter element 11 according to the embodiment of FIG. 5 in that a first pattern substrate 507 of the filter element 17 according to the present embodiment includes a first reinforcing layer 557 and/or a first transmission blocking layer 577, and a second pattern substrate 607 includes a second reinforcing layer 657 and/or a second transmission blocking layer 677.

The first reinforcing layer 557 may be disposed on a side surface of an inner wall of a channel formed by a first patterned layer 537. The first reinforcing layer 557 may be a member for reinforcing a flow of a liquid metal forming a first liquid metal pattern 207. Further, the first reinforcing layer 557 may include a material having hydrophobicity that is greater than that of the first patterned layer 537. The first reinforcing layer 557 may be formed such that a member is disposed on the first patterned layer 537 through a deposition process or the like, or a surface of the first patterned layer 537 is modified through a plasma process or the like.

The first reinforcing layer 557 may be disposed on an upper surface of the first patterned layer 537 in addition to a side surface thereof.

Similarly, the second reinforcing layer 657 may be disposed on a side surface of an inner wall of a channel formed by a second patterned layer 637. The second reinforcing layer 657 may be a member for reinforcing a flow of a liquid metal forming a second liquid metal pattern 307. For example, the second reinforcing layer 657 may include a material having hydrophobicity that is greater than that of the second patterned layer 637. The second reinforcing layer 657 may be formed through a process which is the same as or different from that of the first reinforcing layer 557.

Further, the first transmission blocking layer 577 may be disposed on a first base 517. The first transmission blocking layer 577 may be a member for preventing the liquid metal in a liquid phase from undesirably invading or infiltrating into the first base 517. For example, the first transmission blocking layer 577 may include a material having hydrophobicity that is greater than that of the first base 517 and having liquid permeability that is lower than that thereof. The first transmission blocking layer 577 may be in contact with the first liquid metal pattern 207.

Similarly, the second transmission blocking layer 677 may be disposed on a second base 617. The second transmission blocking layer 677 may include a material having hydrophobicity that is greater than that of the second base 617 and having liquid permeability that is lower than that thereof. The second transmission blocking layer 677 may be in contact with the second liquid metal pattern 307.

The first transmission blocking layer 577 may be disposed to overlap an inductor circuit pattern 217 and a second inductor contact pad 227b and to not overlap a first inductor contact pad 227a. As described above, the first inductor contact pad 227a may be electrically connected to a first capacitor contact pad 327a through the contactor 404. Therefore, the first transmission blocking layer 577 may not be disposed at a portion in which the contactor 404 is formed. Further, the second transmission blocking layer 677 may be disposed to overlap a capacitor circuit pattern 317 and a second capacitor contact pad 327b and to not overlap the first capacitor contact pad 327a. That is, the first transmission blocking layer 577 and the second transmission blocking layer 677 may be disposed to not overlap the contactor 404 in the third direction Z. Meanwhile, as described with reference to FIG. 8, the first contactor 414 and the second contactor 434 have different decrease rates in width.

In some examples, the first liquid metal pattern 207 and/or the second liquid metal pattern 307 may further include conductive particles P dispersed therein. The conductive particles P may be in a state of being substantially uniformly dispersed in the liquid metal which is in a liquid state at room temperature. The conductive particles P may further improve conductivity of the liquid metal.

As described above, the contactor 404 may be made of the liquid metal invading the first base 517 and the second base 617. In this case, a composition of the liquid metal of each of the first contactor 414 and the second contactor 434 may be different from that of the liquid metal of each of the first liquid metal pattern 207 and the second liquid metal pattern 307. For example, the first liquid metal pattern 207 and the second liquid metal pattern 307 may include the conductive particles P, whereas the first contactor 414 and the second contactor 434 may not include the conductive particles P.

A first sealing layer 758 may have a plurality of first holes 758h, and a second sealing layer 768 may have a plurality of second holes 768h. The first hole 758h may overlap the first inductor contact pad 227a and/or the second inductor contact pad 227b, and the second hole 768h may overlap the first capacitor contact pad 327a and/or the second capacitor contact pad 327b. The present invention is not limited thereto, but the liquid metal may be injected through the first hole 758h and/or the second hole 768h.

A first cover member 770 may be disposed on the first hole 758h, and a second cover member 780 may be disposed on the second hole 768h. The first cover member 770 and the second cover member 780 cover the first hole 758h and the second hole 768h, respectively, such that the first liquid metal pattern 207 and the second liquid metal pattern 307, which are provided in the filter element 17, may be prevented from flowing to the outside.

Figure 12:
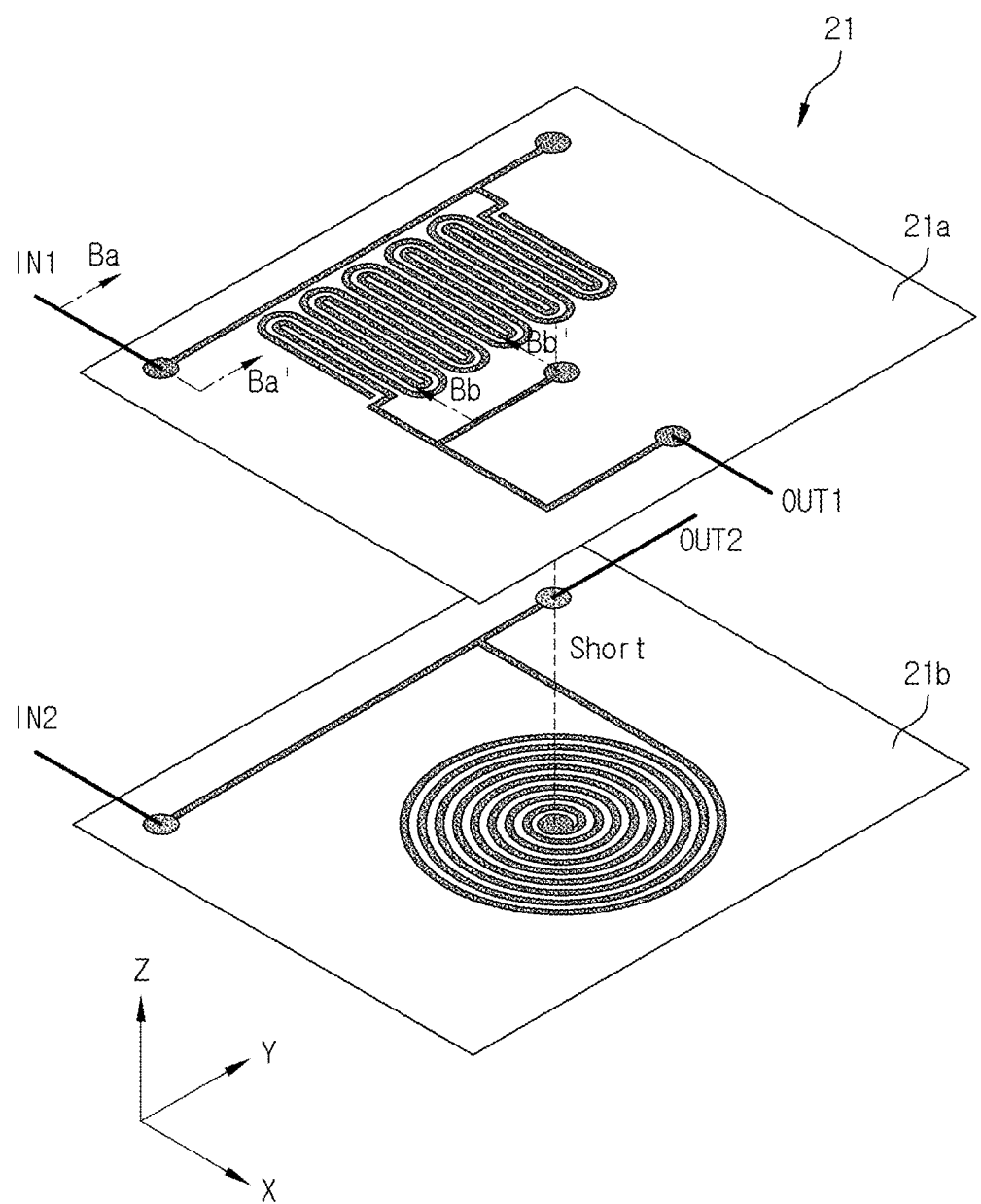
FIG. 12 is an exploded perspective view of the filter element according to still another embodiment of the present invention.
Figure 13:
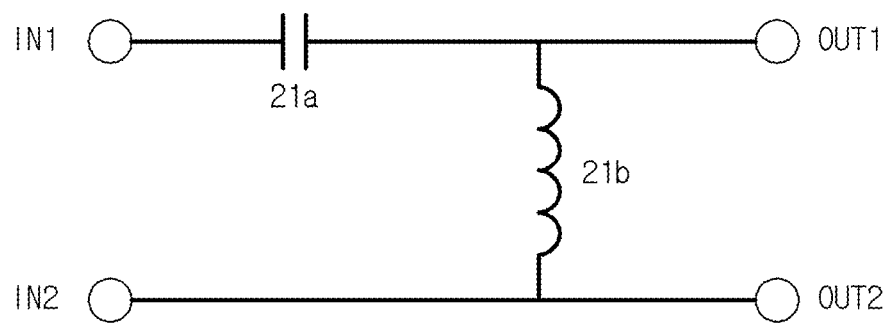
FIG. 13 is a diagram illustrating an equivalent circuit of the filter element of FIG. 12.
Figure 14:
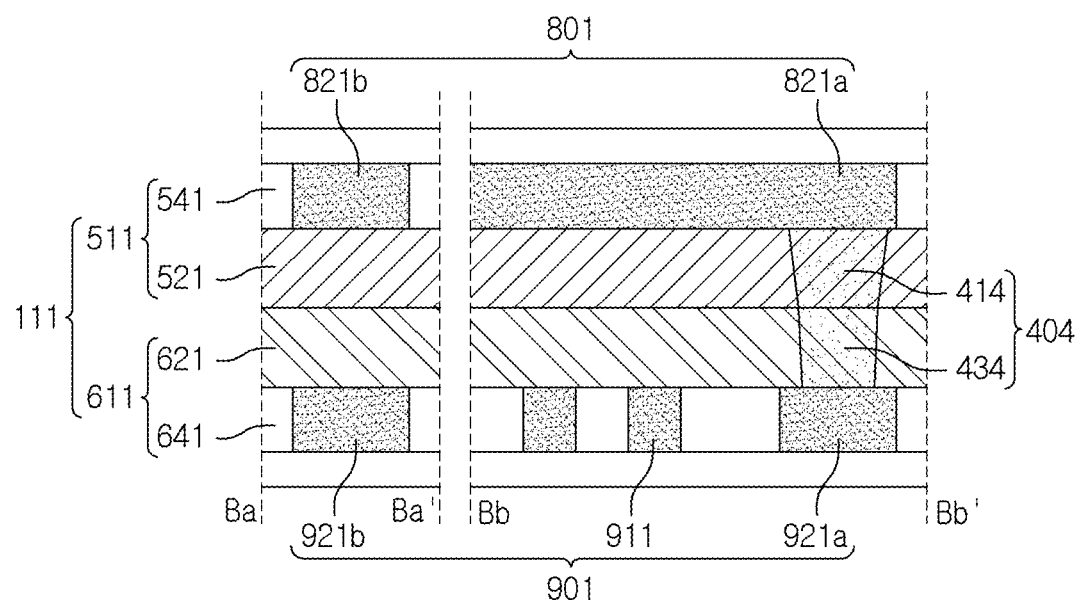
FIG. 14 shows comparative cross-sectional views taken along lines Ba-Ba' and Bb-Bb' of FIG. 12.

FIG. 12 is an exploded perspective view of a filter element 21 according to still another embodiment of the present invention. FIG. 13 is a diagram illustrating an equivalent circuit of the filter element 21 of FIG. 12. FIG. 14 shows comparative cross-sectional views taken along lines Ba-Ba' and Bb-Bb' of FIG. 12.

Referring to FIGS. 12 to 14, the filter element 21 according to the present embodiment includes a capacitor element 21a and an inductor element 21b which are electrically connected to each other. The filter element 21 is a high-pass filter in which a first input terminal IN1 and a first output terminal OUT1 are connected to the capacitor element 21a and in which a second input terminal IN2 and a second output terminal OUT2 are connected to the inductor element 21b, which is different from the filter element 11 according to the embodiment of FIG. 5.

The planar shapes and functions of the capacitor element 21a and the inductor element 21b have been described above, and thus detailed descriptions thereof will be omitted.

In an exemplary example, the capacitor element 21a may be implemented through a first liquid metal pattern 801. The first liquid metal pattern 801 may include a first capacitor contact pad 821a, a second capacitor contact pad 821b, and a capacitor circuit pattern. Further, the inductor element 21b may be implemented through a second liquid metal pattern 901. The second liquid metal pattern 901 may include a first inductor contact pad 921a, a second inductor contact pad 921b, and an inductor circuit pattern 911.

The first capacitor contact pad 821a may be electrically connected to the first inductor contact pad 921a to form a short-circuit node. The first capacitor contact pad 821a may be electrically equivalent to the first output terminal OUT1 of the filter element 21, and the second capacitor contact pad 821b may be electrically equivalent to the first input terminal IN1 of the filter element 21, but the present invention is not limited thereto.

Further, the first inductor contact pad 921a may be electrically connected to the first capacitor contact pad 821a to form a short-circuit node. The second inductor contact pad 921b may be electrically equivalent to the second input terminal IN2 and the second output terminal OUT2 of the filter element 21, but the present invention is not limited thereto.

In an exemplary example, when the filter element 21 is a high-pass filter element, when a portion in which the contactor 404 is in contact with the first liquid metal pattern 801 is electrically equivalent to an output terminal of the high-pass filter element (e.g., the first output terminal IN1), when the first liquid metal pattern 801 constitutes capacitor element 21a, and when the second liquid metal pattern 901 constitutes the inductor element 21b, a width of the contactor 404 may decrease in a direction from the first liquid metal pattern 801 toward the second liquid metal pattern 901. Meanwhile, as described with reference to FIG. 8, the first contactor 414 and the second contactor 434 have different decrease rates in width.

The inductor element is disposed on the upper portion of the above-described filter element 14 according to the embodiment of FIG. 8 and the capacitor element is disposed on the lower portion thereof, whereas according to the present embodiment, the capacitor element 21a is disposed on an upper portion of the filter element 21 and the inductor element 21b is disposed on a lower portion thereof.

However, the filter element 21 according to the present embodiment is equal to the filter element 14 according to the embodiment of FIG. 8 in that the width of the contactor 404 decreases from the upper portion to the lower portion, and liquid permeability of a lower second base 621 is larger than that of an upper first base 521.

In other words, materials of the first base 521 and the second base 621 are determined and a shape of the contactor 404 is designed based on positions of the input terminals and the output terminals of the filter element 21 instead of kinds of passive elements disposed in the upper and lower portions such that the stability of the electrical connection may be improved as in the above description.

Figure 15:
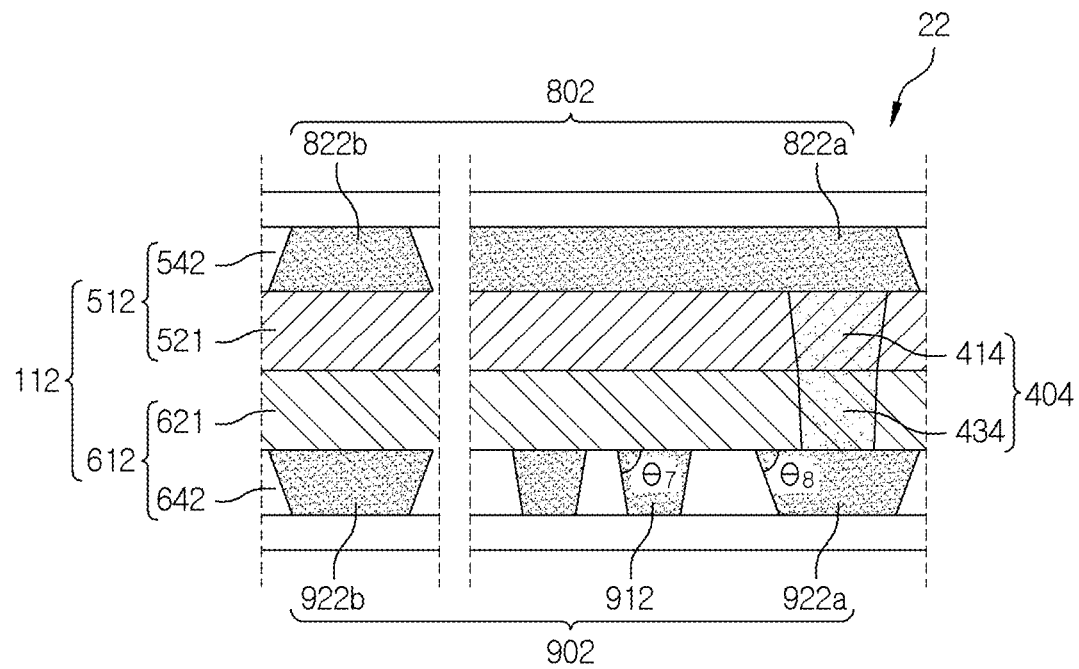
FIG. 15 shows cross-sectional views illustrating a filter element according to still another embodiment of the present invention.

FIG. 15 shows cross-sectional views illustrating a filter element 22 according to still another embodiment of the present invention which is a comparative cross-sectional view illustrating a position corresponding to that of FIG. 5.

Referring to FIG. 15, there is a difference between a filter element 22 according to the present embodiment and the filter element 21 according to the embodiment of FIG. 14 in that side surfaces of a first liquid metal pattern 802 and a second liquid metal pattern 902 are inclined.

In an exemplary example, all side surfaces of a capacitor circuit pattern (not shown), a first capacitor contact pad 822a, and a second capacitor contact pad 822b of the first liquid metal pattern 802 may be inclined. Similarly, all side surfaces of an inductor circuit pattern 912, a first inductor contact pad 922a, and a second inductor contact pad 922b of the second liquid metal pattern 902 may be inclined. In some examples, a seventh inclined angle $\theta_7$ of the side surface of the inductor circuit pattern 912 may be larger than an eighth inclined angle $\theta_8$ of the side surface of the first inductor contact pad 922a.

Therefore, in the filter element 22 according to the present embodiment, the capacitor circuit pattern (not shown) and the inductor circuit pattern 912, which significantly contribute to a current flow, may each be inclined within a range not causing non-uniformity of sheet resistance, thereby stably trapping the liquid metal. Further, the capacitor contact pads 822a and 822b and the inductor contact pads 922a and 922b, which contribute to the electrical connection rather than the current flow, may each be formed to be inclined sufficiently such that there is an effect of improving the electrical connection.

Hereinafter, a method of manufacturing a filter element according to one embodiment of the present invention will be described in detail. FIGS. 16 to 31 are cross-sectional views sequentially illustrating a method of manufacturing a filter element according to one embodiment of the present invention. Hereinafter, an example of a method of manufacturing the filter element 17 according to the embodiment of FIG. 11 will be described with reference to FIGS. 16 to 31, but the present invention is not limited thereto, and a person skilled in the art to which the present invention pertains will also clearly understand a method of manufacturing the filter elements according to other embodiments.

Figure 16:
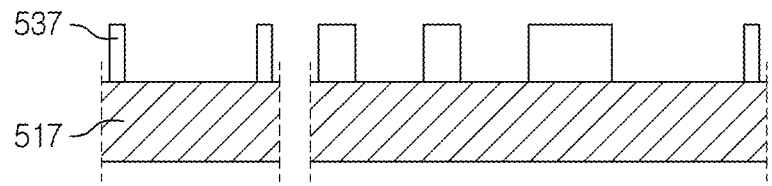
FIGS. 16 to 29 are cross-sectional views sequentially illustrating a method of manufacturing a filter element according to one embodiment of the present invention.

First, referring to FIG. 16, a first patterned layer 537 is formed on a first base 517. The first base 517 may form a first channel or a first trench. A method of forming the first patterned layer 537 is not particularly limited, and the first patterned layer 537 may be formed using a photoresist process, an etching process, a deposition process, or the first patterned layer 537 may be disposed directly. The shape and function of the first patterned layer 537 have been described above, and thus a duplicate description thereof will be omitted.

Figure 17:
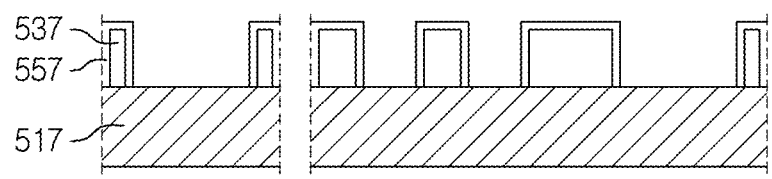

Then, more referring to FIG. 17, the first reinforcing layer 557 is formed on the first patterned layer 537. The first reinforcing layer 557 may be disposed on a side surface and an upper surface of the first patterned layer 537. The shape and function of the first reinforcing layer 557 have been described above, and thus a duplicate description thereof will be omitted.

Figure 18:
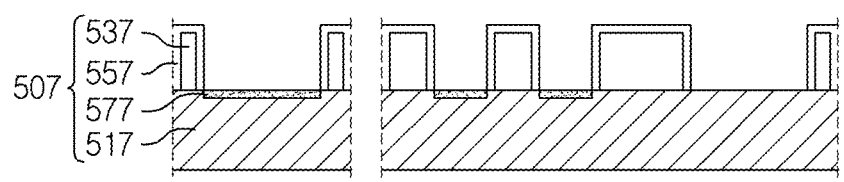

Then, more referring to FIG. 18, the first transmission blocking layer 577 is formed on an exposed surface of the first base 517 to prepare the first pattern substrate 507. The first transmission blocking layer 577 may be formed in only a portion of a channel formed by the first patterned layer 537 and may not be formed in the remaining portion thereof. The shape and function of the first transmission blocking layer 577 have been described above, and thus a duplicate description thereof will be omitted. Through the above-described process, the first pattern substrate 507 having a first channel formed on one surface (an upper surface based on FIG. 18) may be prepared.

Figure 19:
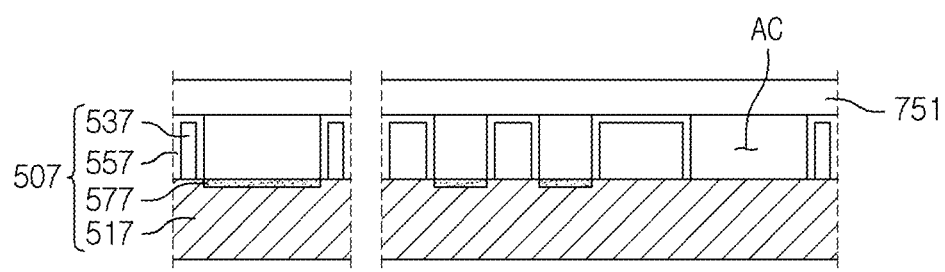

Then, more referring to FIG. 19, a first sealing layer 751 is disposed on the first pattern substrate 507. The first sealing layer 751 may be bonded to the first pattern substrate 507. An air channel AC may be formed between the first sealing layer 751 and the first base 517. In the present operation, the first sealing layer 751 may be formed in a state in which a separate hole is not formed, but the present invention is not limited thereto.

Figure 20:
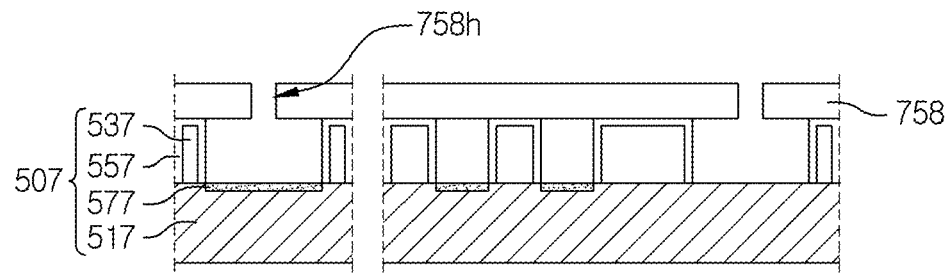

Then, more referring to FIG. 20, the plurality of first holes 758h are formed in the first sealing layer 758. In an exemplary example, some of the plurality of first holes 758h may be formed to overlap the first transmission blocking layer 577, and at least a part of the plurality of first holes 758h may be formed to not overlap the first transmission blocking layer 577. As described above, a contactor may be formed in a region in which the first transmission blocking layer 577 is not formed in a subsequent process.

Figure 21:
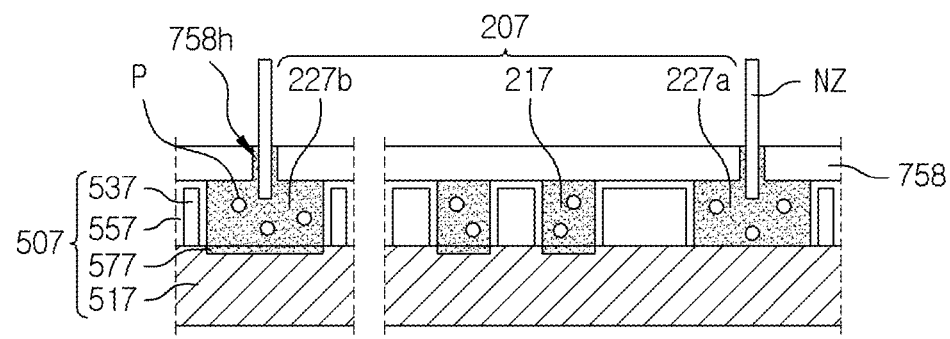

Then, more referring to FIG. 21, a liquid metal injection nozzle NZ is inserted into the first hole 758h and then the first liquid metal pattern 207 is formed in the air channel AC. The first liquid metal pattern 207 may include the conductive particles P. Although not shown in the drawings, in plan view, the first liquid metal pattern 207 may include the inductor circuit pattern 217, the first inductor contact pad 227a, and the second inductor contact pad 227b.

Figure 22:
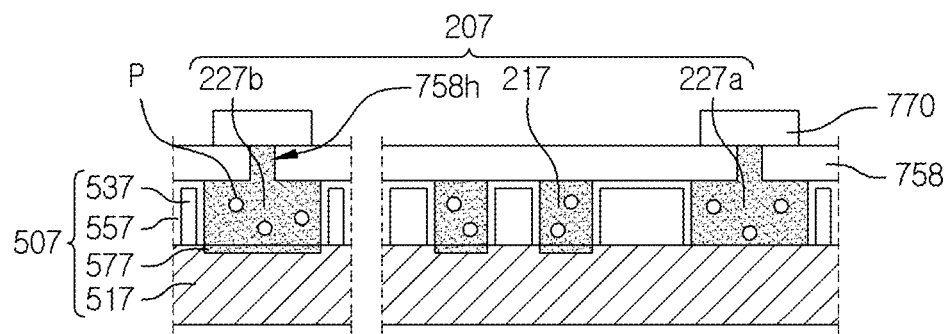

Then, more referring to FIG. 22, the first cover member 770 is disposed on each of the first holes 758h to seal the first liquid metal pattern 207. The first cover member 770 may be disposed to overlap each of the first holes 758h to prevent the first liquid metal pattern 207, which is in a liquid state at room temperature, from flowing out.

Figure 23:
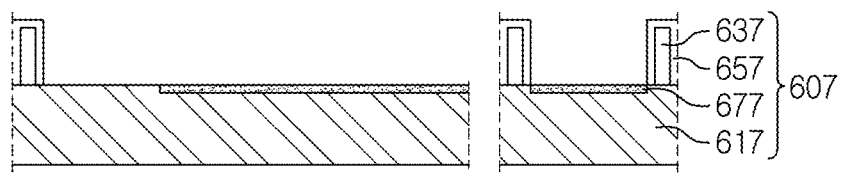

Meanwhile, more referring to FIG. 23, the second patterned layer 637, the second reinforcing layer 657, and the second transmission blocking layer 677 are formed on the second base 617 to prepare the second pattern substrate 607. The second patterned layer 637 may form a second channel or a second trench. The second transmission blocking layer 677 may be formed in only a portion of a channel formed by the second patterned layer 637 and may not be formed in the remaining portion thereof. The shapes and functions of the second base 617, the second patterned layer 637, the second reinforcing layer 657, and the second transmission blocking layer 677 have been described above, and thus duplicate descriptions thereof will be omitted. Through the present operation, the second pattern substrate 607 having a second channel formed on the other surface (an upper surface based on FIG. 23) may be prepared.

Figure 24:
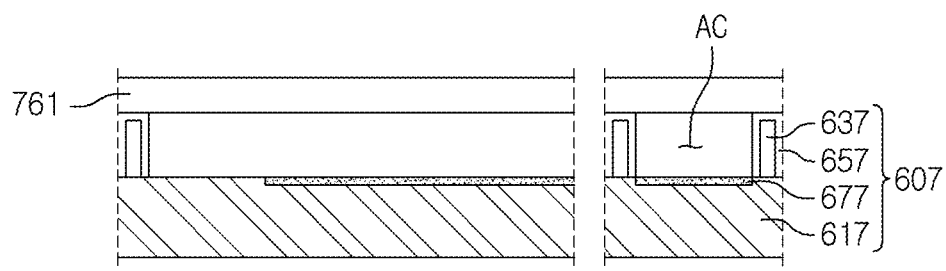

Then, more referring to FIG. 24, a second sealing layer 761 is disposed on the second pattern substrate 607. The second sealing layer 761 may be bonded to the second pattern substrate 607. An air channel AC may be formed between the second sealing layer 761 and the second base 617. In the present operation, the second sealing layer 761 may be in a state in which a separate hole is not formed, but the present invention is not limited thereto.

Figure 25:
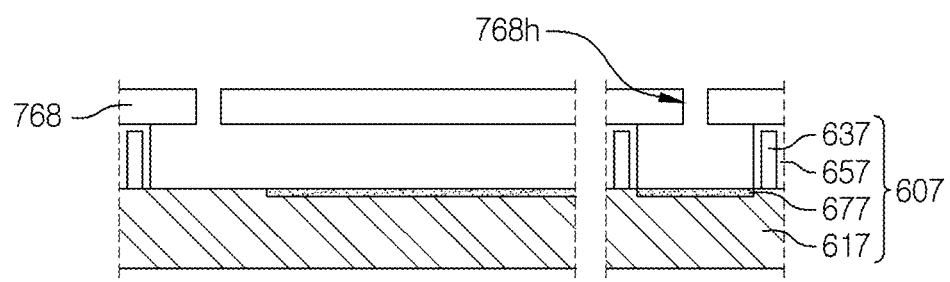

Then, more referring to FIG. 25, the plurality of second holes 768h are formed in the second sealing layer 768. In an exemplary example, some of the plurality of second holes 768h may be formed to overlap the second transmission blocking layer 677, and at least a part of the plurality of second holes 768h may be formed to not overlap the second transmission blocking layer 677. As described above, the contactor may be formed in a region in which the second transmission blocking layer 677 is not formed in a subsequent process. In some examples, the second hole 768h may be formed in a position overlapping the first hole 758h.

Figure 26:
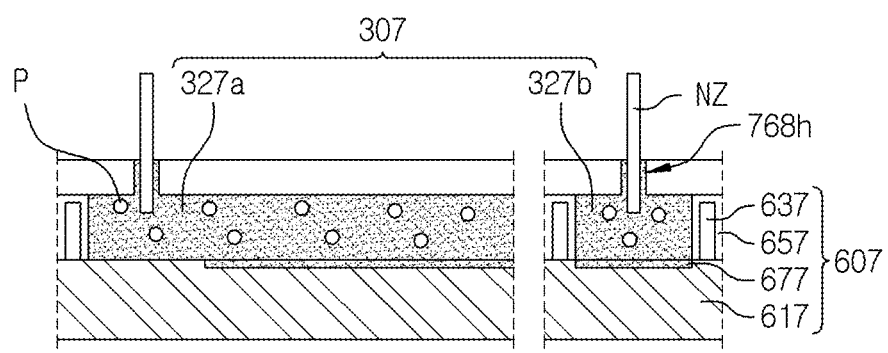

Then, more referring to FIG. 26, the liquid metal injection nozzle NZ is inserted into the second hole 768h and then the second liquid metal pattern 307 is formed in the air channel AC. The second liquid metal pattern 307 may include the conductive particles P. Although not shown in the drawings, in plan view, the second liquid metal pattern 307 may include a capacitor circuit pattern (not shown), the first capacitor contact pad 327a, and the second capacitor contact pad 327b.

Figure 27:
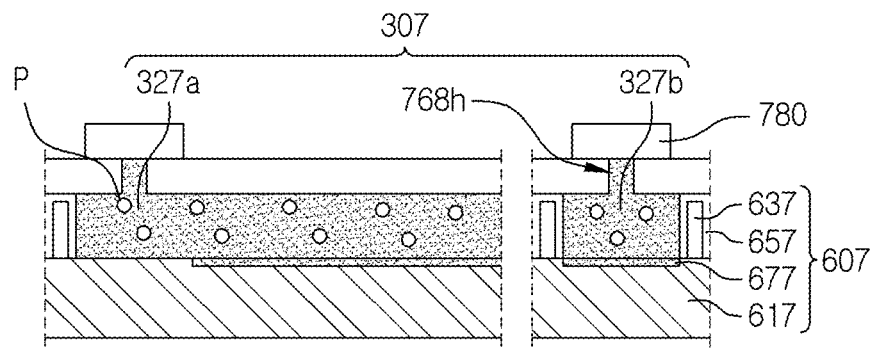

Then, more referring to FIG. 27, the second cover member 780 is disposed on each of the second holes 768h to seal the second liquid metal pattern 307. The second cover member 780 may be disposed to overlap each of the second holes 768h to prevent the second liquid metal pattern 307, which is in a liquid state at room temperature, from flowing out.

Figure 28:
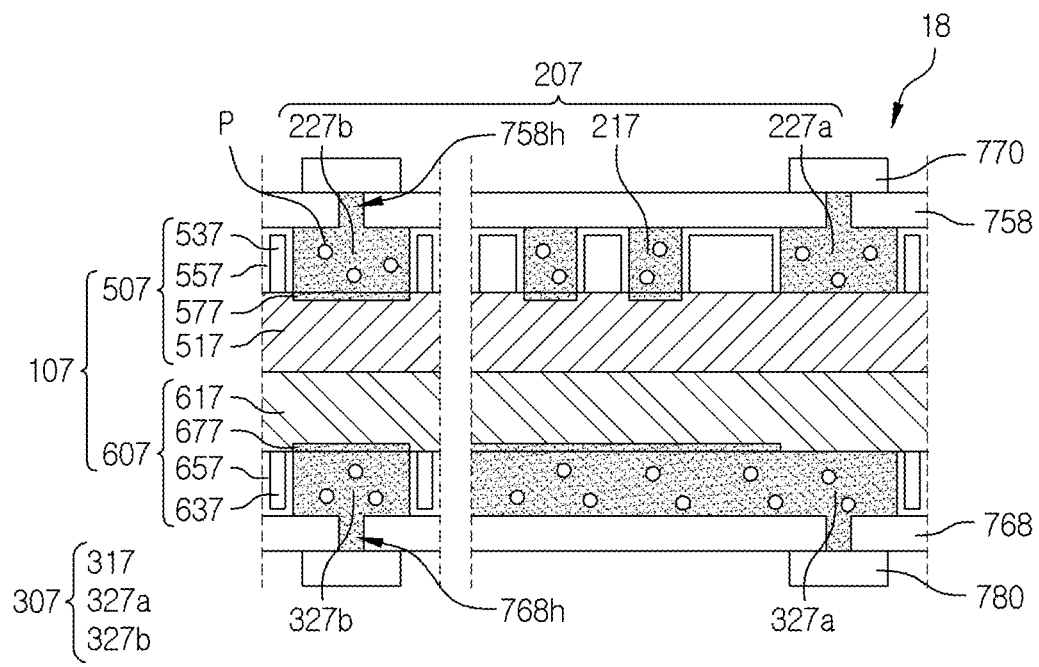

Then, more referring to FIG. 28, one surface of the first pattern substrate 507 (on the basis of FIG. 28, a lower surface) is disposed to face one surface of the second pattern substrate 607 (on the basis of FIG. 28, an upper surface). The first base 517 of the first pattern substrate 507 may be in contact with the second base 617 of the second pattern substrate 607.

In an exemplary example, the first liquid metal pattern 207 on the first pattern substrate 507 and the second liquid metal pattern 307 on the second pattern substrate 607 may be disposed and fixed to have a specific positional relationship. For example, the first inductor contact pad 227a may be disposed to overlap the first capacitor contact pad 327a. For a specific example, the second inductor contact pad 227b may be disposed to overlap the second capacitor contact pad 327b. For a more specific example, the first inductor circuit pattern 217 may be disposed at least partially overlapping the capacitor circuit pattern (not shown). For an even more specific example, a region in which the first transmission blocking layer 577 is not disposed may be disposed at least partially overlapping a region in which the second transmission blocking layer 677 is not disposed.

Figure 29:
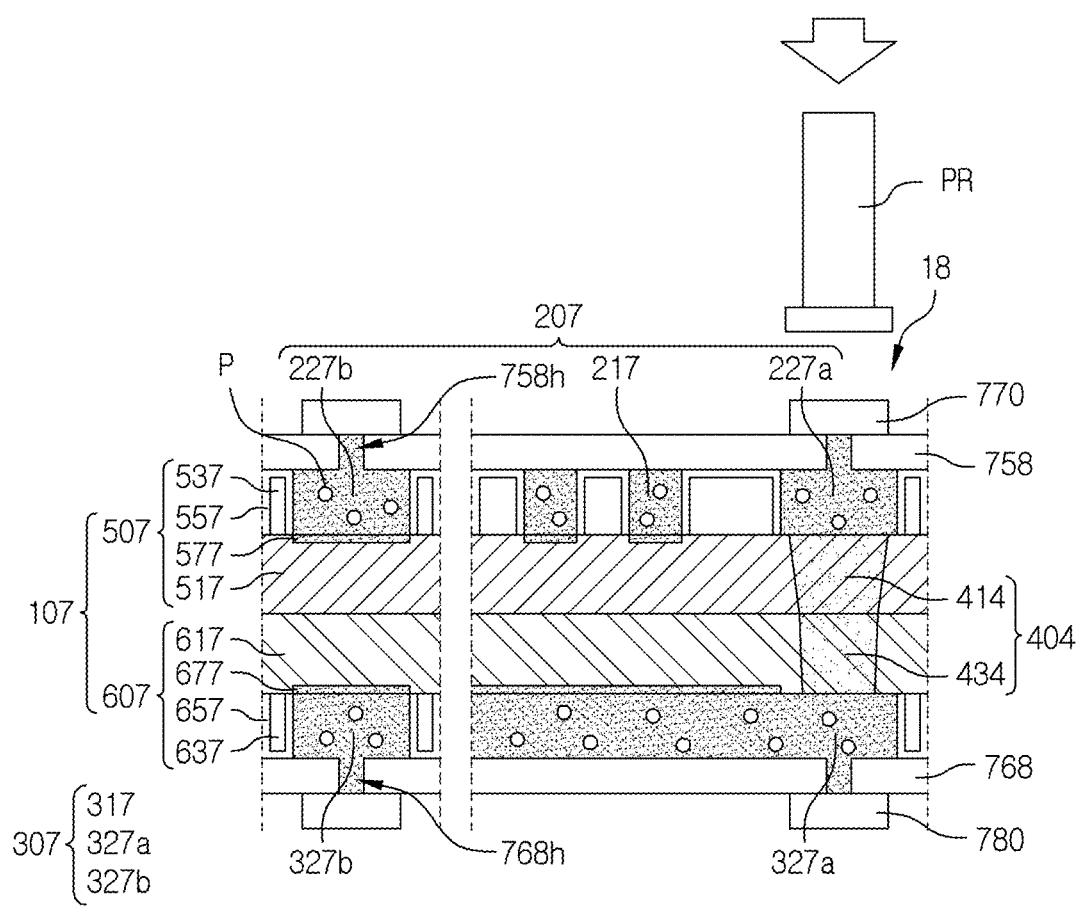

Then, more referring to FIG. 29, a pressure is locally applied to a pattern substrate 107 using a pressurizing member PR to form the contactor 404. The contactor 404 may be formed to invade at least partially in the first base 517 and the second base 617. In an exemplary example, the pressurization may be performed in a direction from the first pattern substrate 507 to the second pattern substrate 607.

As a non-limiting example, when the filter element is a low-pass filter element, the inductor element is disposed on an upper portion of the filter element and the capacitor element is disposed in a lower portion thereof, the pressurization may be performed from the first liquid metal pattern 207 forming the inductor element. In other words, the pressurization may be performed from an upper side to a lower side.

As another non-limiting example, when the filter element is a high-pass filter element, the capacitor element is disposed on an upper portion of the filter element and the inductor element is disposed in a lower portion thereof, the pressurization may be performed from a liquid metal pattern forming the capacitor element. In other words, the pressurization may be performed from an upper side to a lower side.

As shown in FIG. 29, when a low-pass filter element in which the first liquid metal pattern 207 forms an inductor element and the second liquid metal pattern 307 forms a capacitor element, a portion in which the first contactor 414 is in contact with the first liquid metal pattern 207 may be electrically equivalent to an output terminal (e.g., a first output terminal).

In this case, the pressurization is performed in a direction from the first liquid metal pattern 207 to the second liquid metal pattern 307 such that the width of the contactor 404 may be formed to decrease in the direction from the first liquid metal pattern 207 to the second liquid metal pattern 307. Consequently, as described above, the electrical connection of the filter element may be improved, and the load applied to the output terminal may be reduced.

Further, when the first base 517 and the second base 617 have different liquid permeabilities, specifically, the second base 617 has liquid permeability that is larger than that of the first base 517, it may be configured such that a decrease rate in width of the first contactor 414 is larger than a decrease rate in width of the second contactor 434. Consequently, contact resistance between the second contactor 434 and the second liquid metal pattern 307 may be lowered, and it is possible to induce a smooth electrical connection between the first liquid metal pattern 207 and the second liquid metal pattern 307.

That is, the method of manufacturing a filter element according to the present embodiment is capable of forming an electrical connection path between the first liquid metal pattern 207 and the second liquid metal pattern 307 without forming a separate via hole for an electrical connection between the upper and lower portions in the first base 517 and the second base 617. Therefore, there is an effect of reducing a manufacturing cost and simplifying a process. Further, the present invention is not limited thereto, and the shape of the contactor 404 may be controlled using the liquid permeabilities of the first base 517 and the second base 617. Furthermore, a shape and a width of a portion in which the contactor 404 is in contact with the first liquid metal pattern 207, and a shape and a width of a portion in which the contactor 404 is in contact with the second liquid metal pattern 307 may be controlled using the liquid permeabilities. The filter element with an improved electrical connection between the inductor element and the capacitor element may be manufactured.

Hereinafter, the present invention will be described in more detail with reference to Examples and Comparative Examples.

EXAMPLE 1-1: MANUFACTURING OF INDUCTOR ELEMENT

Figure 34A:
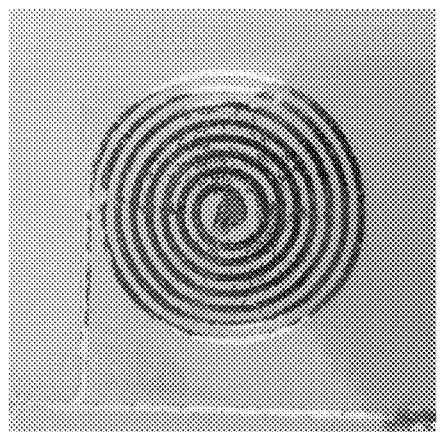
FIG. 34A shows a photograph of an inductor element according to Example 1-1.

An inductor element having a shape shown in FIG. 34A was manufactured. A mixed composition of gallium and indium was used as a liquid metal. A cross-sectional shape of the inductor element may be clearly predicted by those skilled in the art to which the present invention pertains. A paper material having predetermined transmission was used as a first base.

Figure 30:
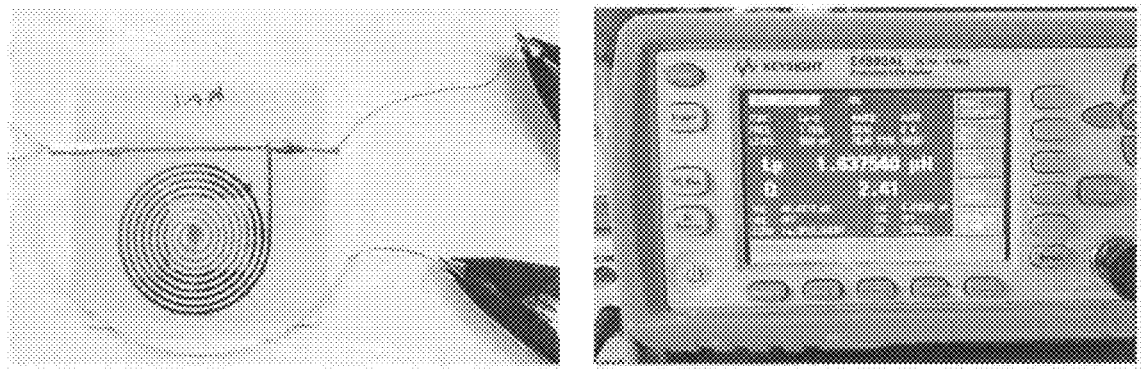
FIG. 30 shows photographs of a characteristic measurement of an inductor element according to Example 1-1.

Further, a characteristic of the inductor element was measured and shown in FIG. 30. Referring to FIG. 30, it can be confirmed that the inductor element according to Example 1-1 exhibited inductance of 1.63 pH.

EXAMPLE 1-2: MANUFACTURING OF CAPACITOR ELEMENT

Figure 34B:
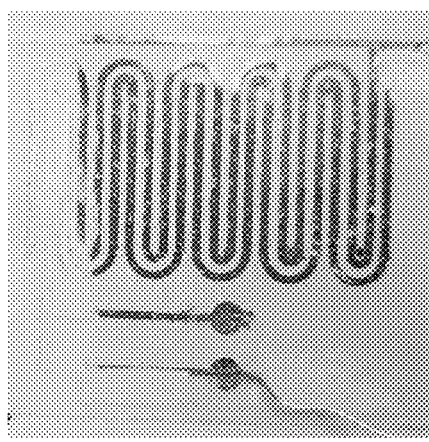
FIG. 34B shows photographs of a capacitor element according to Example 1-2.

A capacitor element having a shape shown in FIG. 34B was manufactured. A mixed composition of gallium and indium was used as a liquid metal. A cross-sectional shape of the capacitor element may be clearly predicted by those skilled in the art to which the present invention pertains. A paper material having predetermined transmission was used as a second base.

Figure 31:
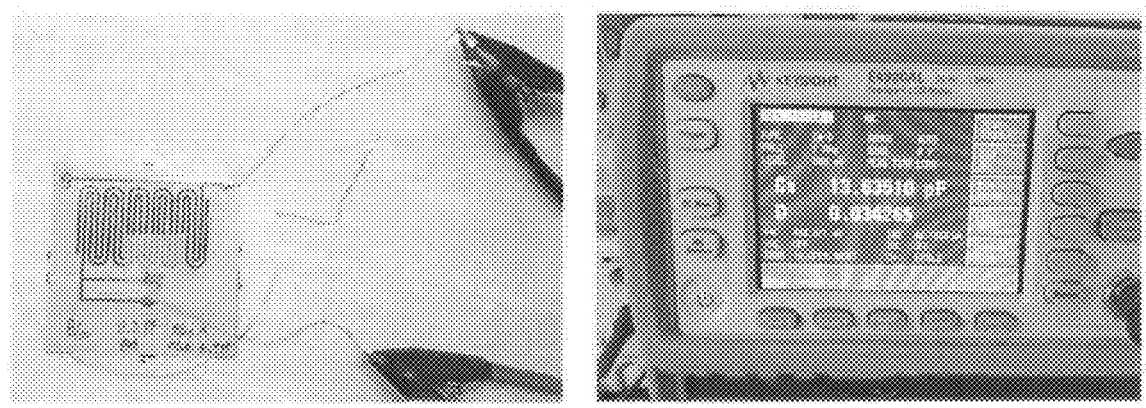
FIG. 31 shows photographs of a characteristic measurement of a capacitor element according to Example 1-2.

Further, a characteristic of the capacitor element was measured and shown in FIG. 31. Referring to FIG. 31, it can be confirmed that the capacitor element according to Example 1-2 exhibited capacitance of 13.6 pF.

Comparative Example 1: Manufacturing of Comparative Inductor Element

Figure 35A:
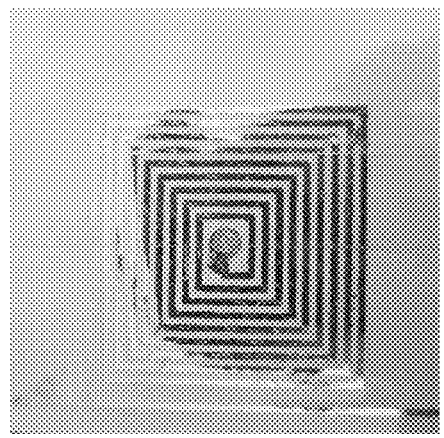
FIG. 35A shows a photograph of an inductor element according to Comparative Example 1.

An inductor element was manufactured in the same manner as in Example 1-1 except for modifying a shape of the inductor element as shown in FIG. 35A.

In the case of Comparative Example 1, it was confirmed that, although an angled pattern portion was not completely filled with the liquid metal during an injection process of the liquid metal, a pattern was damaged due to an excessive rise of a pressure in a channel, and the liquid metal was leaked.

Comparative Example 2: Manufacturing of Comparative Capacitor Element

Figure 35B:
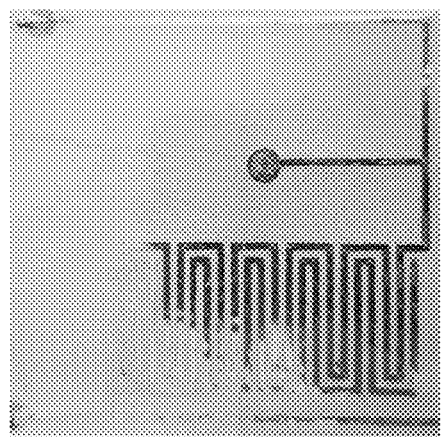
FIG. 35B shows photographs of a capacitor element according to Comparative Example 2.

A capacitor element was manufactured in the same manner as in Example 1-2, except for modifying a shape of the capacitor element as shown in FIG. 35B.

In the case of Comparative Example 2, it was confirmed that a problem occurred during an injection process of the liquid metal as in Comparative Example 1.

EXAMPLE 2-1: MANUFACTURING OF LOW-PASS FILTER ELEMENT

The low-pass filter element as shown in FIGS. 1 and 2 was implemented using the inductor element and the capacitor element according to Example 1-1 and Example 1-2. Specifically, a contact pad of the inductor element was disposed to overlap a contact pad of the capacitor element, and a pressure of 10 kgf was applied for 10 seconds to electrically connect the inductor element to the capacitor element.

Figure 32:
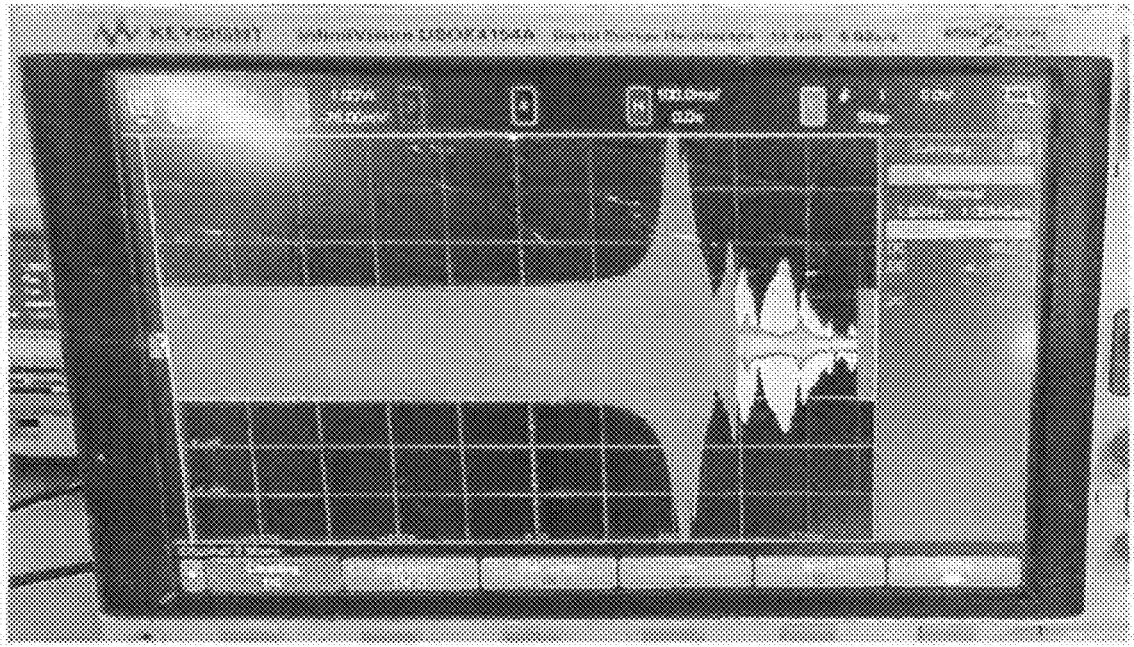
FIG. 32 shows a photograph of a characteristic measurement of a low-pass filter element according to Example 2-1.

Further, a characteristic of the low-pass filter element was measured and shown in FIG. 32. Low-pass filter element characteristic measurement conditions were as follows.

Sweep Mode: Log scale
Sweep Time: 1 second
Start Frequency: 100 Hz
End Frequency: 50 MHz Referring to FIG. 32, it can be confirmed that the low-pass filter element according to Example 2-1 had a low-pass filter characteristic.

EXAMPLE 2-2: MANUFACTURING OF HIGH-PASS FILTER ELEMENT

The high-pass filter element as shown in FIGS. 12 and 13 was implemented using the inductor element and the capacitor element according to Example 1-1 and Example 1-2. Specifically, a contact pad of the inductor element was disposed to overlap a contact pad of the capacitor element, and a pressure of 10 kgf was applied for 10 seconds to electrically connect the inductor element to the capacitor element.

Figure 33:
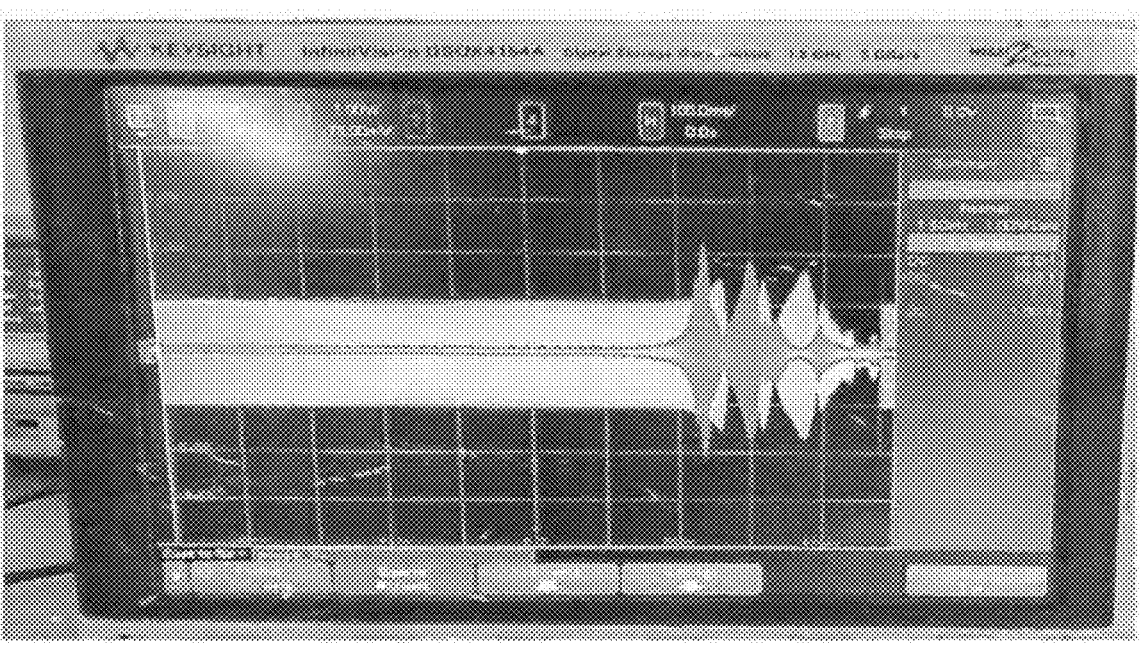
FIG. 33 shows a photograph of a characteristic measurement of a high-pass filter element according to Example 2-2.

Further, a characteristic of the high-pass filter element was measured and shown in FIG. 33. High-pass filter element characteristic measurement conditions were the same as in Example 2-1. Referring to FIG. 33, it can be confirmed that the high-pass filter element according to Example 2-2 had a high-pass filter characteristic.

In accordance with the embodiments of the present invention, it is possible to provide a filter element having excellent flexibility and an improved electrical connection between passive elements through a stable structure, and a method of manufacturing the same.

While the present invention has been particularly illustrated and described with reference to exemplary embodiments thereof, it will be understood by those of ordinary skill in the art that various changes in form and detail may be made therein without departing from the spirit and scope of the present invention as defined by the following claims. The exemplary embodiments should be considered in a descriptive sense only and not for purposes of limitation.

What is claimed is:

1. A filter element comprising:
a pattern substrate having a first channel formed on one surface and a second channel formed on the other surface and including a first base and a second base which have different liquid permeabilities;
a first liquid metal pattern disposed in the first channel;
a second liquid metal pattern disposed in the second channel and at least partially overlapping the first liquid metal pattern; and
a contactor configured to invade in the first base and the second base and electrically connect the first liquid metal pattern to the second liquid metal pattern.

2. The filter element of claim 1, wherein:
the contactor is electrically equivalent to an output terminal of the filter element;
a width of the contactor decreases in a direction from a first area at which the first liquid metal pattern is connected to the contactor to a second area at which the second liquid metal pattern is connected to the contactor, and
the direction is a view direction of a plan view.

3. The filter element of claim 2, wherein:
the filter element is a low-pass filter element;
the first liquid metal pattern forms an inductor element; and
the second liquid metal pattern forms a capacitor element.

4. The filter element of claim 2, wherein:
the filter element is a high-pass filter element;
the first liquid metal pattern forms a capacitor element; and
the second liquid metal pattern forms an inductor element.

5. The filter element of claim 2, wherein:
the first base is in contact with the first liquid metal pattern;
the second base is in contact with the second liquid metal pattern;
the contactor includes:
a first contactor configured to invade in the first base; and
a second contactor configured to invade in the second base and having a physical boundary with the first contactor; and
a variance rate in width of the first contactor is greater than that in width of the second contactor.

6. The filter element of claim 5, wherein:
each of the first liquid metal pattern and the second liquid metal pattern includes conductive particles dispersed therein; and
the first contactor and the second contactor have compositions different from those of the first liquid metal pattern and the second liquid metal pattern.

7. The filter element of claim 6, wherein:
the first liquid metal pattern includes a first contact pad and a first circuit pattern connected to the first contact pad; and
the second liquid metal pattern includes a second contact pad overlapping the first contact pad and the contactor, and a second circuit pattern connected to the second contact pad and at least partially overlapping the first circuit pattern.

8. The filter element of claim 7, wherein each of the first circuit pattern and the second circuit pattern has a round shape in the plan view.

9. The filter element of claim 8, wherein the pattern substrate further includes:
a first patterned layer disposed on one surface of the first base;
a second patterned layer disposed on one surface of the second base; and
a reinforcing layer disposed on a side surface of the first patterned layer.

10. The filter element of claim 9, wherein:
the pattern substrate further includes a transmission blocking layer disposed on the one surface of the first base and configured to be in contact with the first liquid metal pattern; and
the transmission blocking layer overlaps the first circuit pattern and does not overlap the first contact pad.

11. The filter element of claim 10, further comprising:
a sealing layer disposed on the one surface of the pattern substrate and having a plurality of holes overlapping the first contact pad; and
a plurality of cover members disposed on the plurality of holes of the sealing layer to cover the plurality of holes and configured to be in contact with the first liquid metal pattern,
wherein at least a part of the plurality of holes and at least a part of the plurality of cover members are disposed to not overlap the transmission blocking layer.

12. The filter element of claim 8, wherein:
each of a side surface of the first contact pad and a side surface of the first circuit pattern has an inclination angle of less than 90 degrees;

a maximal width of the first contact pad is greater than that of the first circuit pattern; and an inclination angle of the first circuit pattern is greater than that of the first contact pad.

13. A filter element comprising:

a first base;

a first passive element disposed on one surface of the first base;

a second base disposed on the other surface of the first base and having liquid permeability that is greater than that of the first base;

a second passive element disposed on the second base;

a first contactor formed by a liquid metal invading in the first base and configured to be electrically connected to the first passive element; and a second contactor formed by a liquid metal invading in the second base and configured to be electrically connected to the first contactor and the second passive element, wherein an average width of the first contactor is greater than that of the second contactor.

14. A method of preparing a filter element, comprising:

preparing a first pattern substrate having a first channel formed on one surface thereof and comprising a first base;

forming a first liquid metal pattern in the first channel;

preparing a second pattern substrate having a second channel formed on one surface thereof and comprising a second base;

forming a second liquid metal pattern in the second channel;

disposing the other surface of the first pattern substrate to face the other surface of the second pattern substrate; and pressurizing a portion of the first liquid metal pattern to form a contactor invading in the first base and the second base.

15. The method of claim 14, wherein:

the pressurization is performed in a direction from the first pattern substrate to the second pattern substrate; and liquid permeability of the second base is greater than that of the first base.

16. The method of claim 15, further comprising, between the preparing of the first pattern substrate and the forming of the first liquid metal pattern, disposing a sealing layer on the one surface of the first pattern substrate; and forming a hole in the sealing layer.

17. The method of claim 16, wherein the preparing of the first pattern substrate includes:

preparing the first base;

forming a first patterned layer, which forms the first channel, on the one surface of the first base;

forming a reinforcing layer on a side surface of the first patterned layer;

forming a transmission blocking layer on the one surface of the first base which is exposed without being covered by the first patterned layer, wherein the forming of the first liquid metal pattern includes injecting a liquid metal through the hole of the sealing layer.

* * * * *